(12) United States Patent
Tamura et al.

(10) Patent No.: US 10,835,103 B2
(45) Date of Patent: Nov. 17, 2020

(54) ENDOSCOPE ILLUMINATION APPARATUS AND ENDOSCOPE SYSTEM

(71) Applicant: OLYMPUS CORPORATION, Tokyo (JP)

(72) Inventors: Kazuaki Tamura, Hachioji (JP); Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 214 days.

(21) Appl. No.: 16/009,340

(22) Filed: Jun. 15, 2018

(65) Prior Publication Data

US 2018/0303312 A1    Oct. 25, 2018

Related U.S. Application Data

(63) Continuation of application No. PCT/JP2015/085359, filed on Dec. 17, 2015.

(51) Int. Cl.
*A61B 1/00* (2006.01)
*A61B 1/04* (2006.01)
(Continued)

(52) U.S. Cl.
CPC ...... *A61B 1/00006* (2013.01); *A61B 1/00057* (2013.01); *A61B 1/00096* (2013.01);
(Continued)

(58) Field of Classification Search
CPC .... A61B 1/00006; A61B 1/0638; A61B 1/043
(Continued)

(56) References Cited

U.S. PATENT DOCUMENTS

| | | | |
|---|---|---|---|
| 8,939,628 B2 | 1/2015 | Ito et al. | |
| 2007/0147033 A1 | 6/2007 | Ogawa et al. | |
| 2010/0274090 A1* | 10/2010 | Ozaki | A61B 1/00096 600/173 |
| 2013/0342110 A1 | 12/2013 | Yamamoto et al. | |

(Continued)

FOREIGN PATENT DOCUMENTS

| | | | |
|---|---|---|---|
| JP | 2007-175433 A | 7/2007 |
| JP | 2008-004419 A | 1/2008 |

(Continued)

OTHER PUBLICATIONS

International Search Report dated Mar. 15, 2016 issued in PCT/JP2015/085359.
English Abstract of JP 2008-122838, dated May 29, 2008.
International Preliminary Report and Written Opinion dated Jun. 28, 2018 received in PCT/JP2015/085359.
(Continued)

*Primary Examiner* — Jeffery A Williams
(74) *Attorney, Agent, or Firm* — Scully, Scott, Murphy & Presser, P.C.

(57) ABSTRACT

An endoscope illumination apparatus includes a light convertor including first and second light conversion members that receive primary light emitted from a primary light source and convert at least one of the optical properties of the primary light, a detector that receives at least part of first light conversion light converted by the first light conversion member as detection light, and outputs a detection signal corresponding to a quantity of the detection light, and an operation estimation circuit that estimates, based on an amount of change in the detection signal output from the detector, whether any one of the first and second light conversion members is in an abnormal operation or both of the first and second light conversion members are in an abnormal operation.

20 Claims, 10 Drawing Sheets

(51) Int. Cl.
*A61B 1/06* (2006.01)
*H04N 5/225* (2006.01)
*H04N 5/232* (2006.01)
*A61B 1/07* (2006.01)
*A61B 1/045* (2006.01)
*H04N 5/351* (2011.01)
*H04N 5/378* (2011.01)

(52) U.S. Cl.
CPC .......... *A61B 1/00126* (2013.01); *A61B 1/043* (2013.01); *A61B 1/045* (2013.01); *A61B 1/0653* (2013.01); *A61B 1/07* (2013.01); *H04N 5/2256* (2013.01); *H04N 5/232* (2013.01); *H04N 5/351* (2013.01); *H04N 5/378* (2013.01); *H04N 2005/2255* (2013.01)

(58) Field of Classification Search
USPC .......................................................... 348/69
See application file for complete search history.

(56) References Cited

U.S. PATENT DOCUMENTS

| | | | |
|---|---|---|---|
| 2014/0016345 A1* | 1/2014 | Nishio | .................. G01J 1/0271 362/552 |
| 2015/0327755 A1* | 11/2015 | Daidoji | ................ A61B 1/0638 600/476 |

FOREIGN PATENT DOCUMENTS

| | | |
|---|---|---|
| JP | 2011-258610 A | 12/2011 |
| JP | 2012-179225 A | 9/2012 |
| JP | 2012-208258 A | 10/2012 |
| JP | 5103874 B2 | 12/2012 |
| JP | 2014-174192 A | 9/2014 |

OTHER PUBLICATIONS

Japanese Office Action dated Jul. 16, 2019 in Japanese Patent Application No. 2017-556275.

* cited by examiner

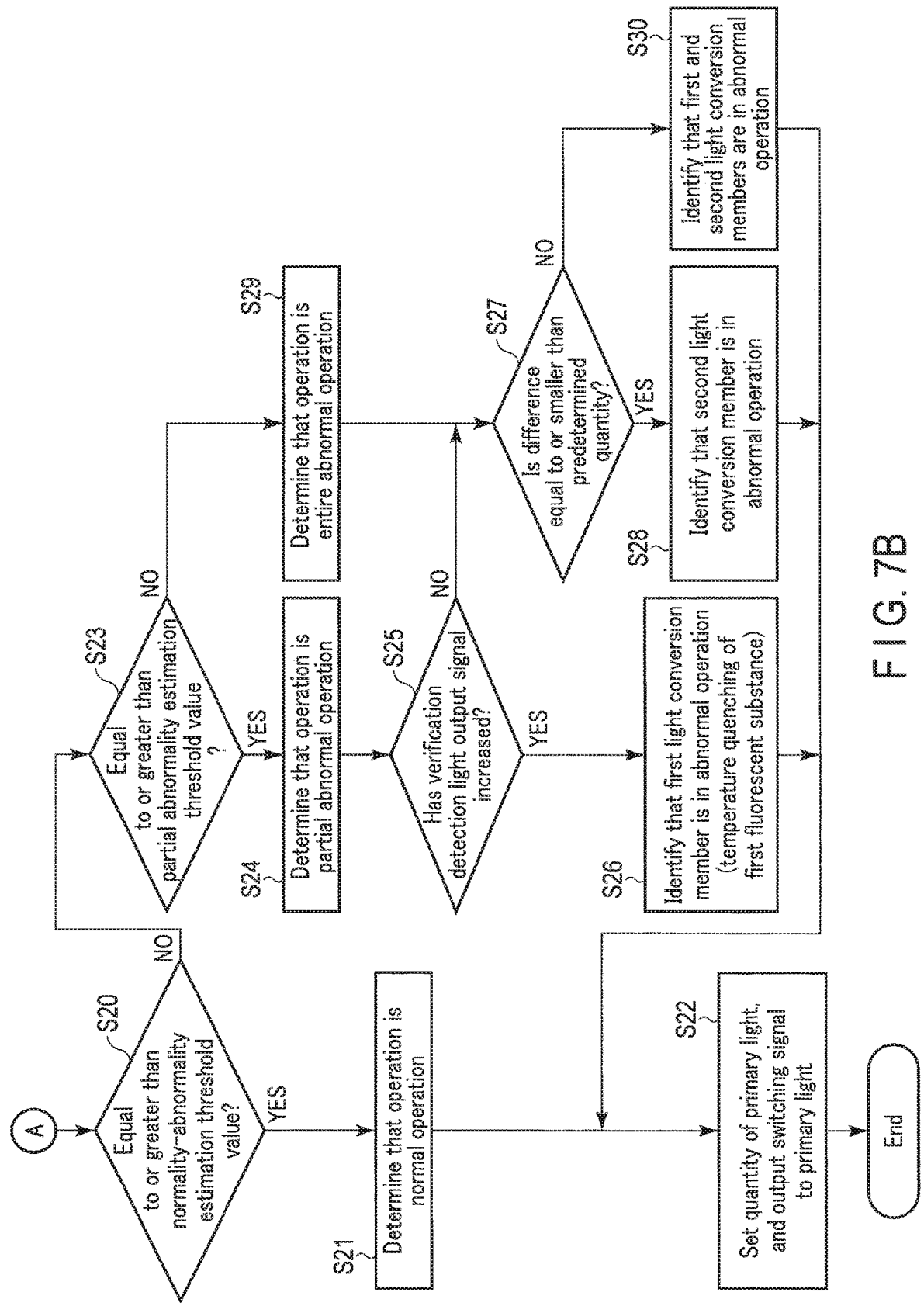
F I G. 7B

ENDOSCOPE ILLUMINATION APPARATUS AND ENDOSCOPE SYSTEM

CROSS-REFERENCE TO RELATED APPLICATIONS

This application is a Continuation Application of PCT Application No. PCT/JP2015/085359, filed Dec. 17, 2015, the entire contents of which are incorporated herein by reference.

BACKGROUND OF THE INVENTION

1. Field of the Invention

The present invention relates to an endoscope illumination apparatus and an endoscope system including the endoscope illumination apparatus.

2. Description of the Related Art

Conventionally, fiber light sources have been offered in which light from a small solid-state light source is wavelength-converted by a wavelength conversion member disposed at the tip end of an optical fiber to change the light to a desired irradiation pattern or color.

For example, Japanese Patent No. 5103874 discloses the following light emitting apparatus. In other words, the light emitting apparatus includes a light source, a light guide member optically connected to the light source, a wavelength conversion member disposed at an exit end portion of the light guide member, and a detection member including a light receiving element that detects return light from the wavelength conversion member.

BRIEF SUMMARY OF THE INVENTION

An endoscope illumination apparatus includes a light convertor including first and second light conversion members that receive primary light emitted from a primary light source and convert at least one of the optical properties of the primary light, a detector that receives at least part of first light conversion light converted by the first light conversion member as detection light, and outputs a detection signal corresponding to a quantity of the detection light, the detector including a light quantity sensor, and an operation determination circuit including an operation estimation circuit that estimates, based on an amount of change in the detection signal output from the detector, whether any one of the first and second light conversion members is in an abnormal operation or both of the first and second light conversion members are in an abnormal operation.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 7B is a diagram showing the remaining part of the flowchart for explaining the operation of the operation determination circuit.

DETAILED DESCRIPTION OF THE INVENTION

Hereinafter, modes for carrying out the present invention will be described with reference to the drawings.

First Embodiment

Figure 1:
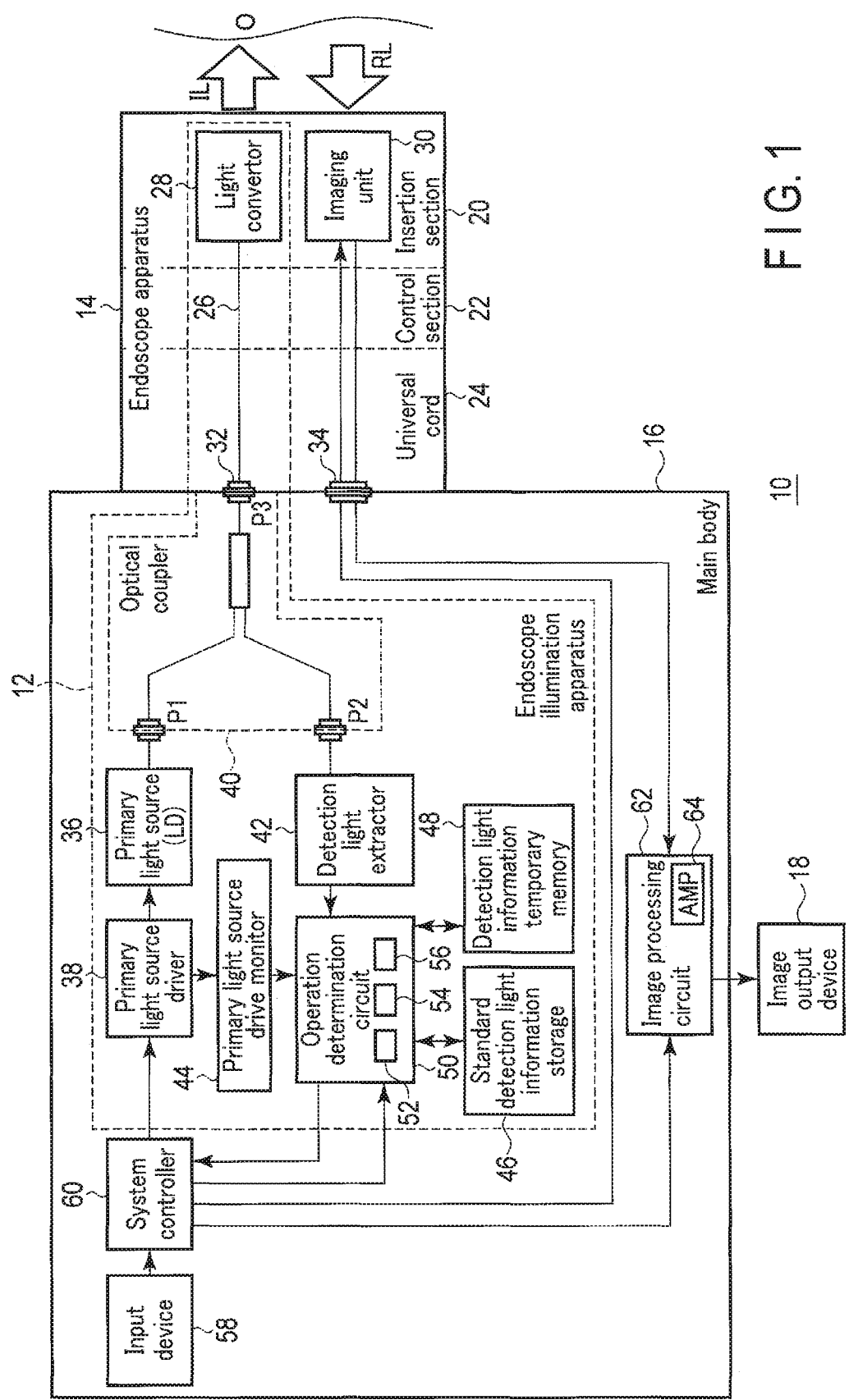
FIG. 1 is a block diagram showing a schematic constitution of an endoscope system according to an embodiment of the present invention including an endoscope illumination apparatus according to an embodiment of the present invention.

FIG. 1 is a diagram showing a schematic constitution of an endoscope system 10 according to an embodiment of the present invention including an endoscope illumination apparatus 12 according to a first embodiment of the present invention. The endoscope system 10 according to the present embodiment includes an endoscope apparatus 14, a main body (video processor) 16, and an image output device (monitor) 18. The endoscope illumination apparatus 12 according to the present embodiment applies illumination light IL to an object O, and its components are distributed to the endoscope apparatus 14 and a main body 16, as will be described in detail later.

In this specification, the endoscope apparatus refers not only to a medical endoscope apparatus (an upper digestive tract endoscope apparatus, a large intestine endoscope apparatus, an ultrasonic endoscope apparatus, a cystoscope apparatus, a pyeloscope apparatus, a bronchoscope apparatus, etc.) and an industrial endoscope apparatus, but also generally to a device having an insertion section to be inserted into the object O. Hereinafter, the medical endoscope apparatus will be described as an example of the endoscope apparatus 14. In this case, the object O is an affected part, a diseased part, or the like in a body (for example, within a body cavity (lumen)) of a patient or the like.

The endoscope apparatus 14 includes an elongated insertion section 20 to be inserted into a object O, a control section 22 connected to the base end portion of the insertion section 20, a universal cord 24 connecting the control section 22 and the main body 16. The endoscope apparatus 14 is a tubular insertion apparatus for inserting the tubular insertion section 20 into a body cavity.

Although not specifically shown, the insertion section 20 has a distal end hard section, a bendable section, and a flexible tube section from the tip end portion side to the base end portion side of the insertion section 20 are doing. Here, the base end portion of the distal end hard section is connected to the tip end portion of the bendable section, and the base end portion of the bendable section is connected to the tip end portion of the flexible tube section. The distal end hard section is a tip end portion of the insertion section 20 and a tip end portion of the endoscope apparatus 14 and is a hard member. The bendable section bends in a desired direction in response to an operation of the control section 22 by a user (an operator such as a doctor). Due to the curvature of the bendable section, the position and direction of the distal end hard section are changed, and the object O is captured in the observation visual field. The object O captured in this way is irradiated with the Illumination light IL from the endoscope illumination apparatus 12, and the object O is illuminated. The flexible tube section is a tubular member having a desired flexibility and bending by receiving an external force.

The endoscope apparatus 14 includes the insertion section 20, the control section 22, and an optical fiber 26 extending in the universal cord 24. This optical fiber 26 is a component of the endoscope illumination apparatus 12. Further, the endoscope apparatus 14 includes a light convertor 28, which is also a component of the endoscope illumination apparatus 12, in the distal end hard section of the insertion section 20. The tip end portion of the optical fiber 26 is optically connected to the light convertor 28. Details of the light convertor 28 will be described later.

The endoscope apparatus 14 further includes in the distal end hard section of the insertion section 20 an imaging unit 30 that detects reflected light RL of the illumination light IL with which the object O is irradiated and outputs an imaging signal. The imaging unit 30 receives the reflected light RL from the object O irradiated by the endoscope illumination apparatus 12 and performs imaging. Specifically, it is a CCD imager or CMOS imager.

For the main body 16 and the universal cord 24 of the endoscope apparatus 14, the universal cord 24 is attachable to and detachable from the main body 16 by a connector portion. The connector portion includes an optical connector 32 for optically connecting the base end of the optical fiber 26 connected to the light convertor 28 to the main body 16, and an electrical connector 34 for optically connecting electric wiring connected to the imaging unit 30 to the main body 16.

The components allocated in the main body 16 of the endoscope illumination apparatus 12 includes a primary light source 36, a primary light source driver 38, an optical coupler 40, a detection light extractor 42, a primary light source drive monitor 44, a standard detection light information storage 46, a detection light information temporary memory 48, and an operation determination circuit 50. The operation determination circuit 50 includes an operation estimation circuit 52, an abnormal operation determination circuit 54, and an abnormal operation member identification circuit 56. Details of these parts will be described later.

It is a matter of course that allocation of these components to the endoscope apparatus 14 and the main body 16 is not limited to this. For example, the optical coupler 40 may also be disposed in (the control section 22 of) the endoscope apparatus 14. Alternatively, both the primary light source 36 and the optical coupler 40, or the primary light source 36, the optical coupler 40, and the detection light extractor 42 can be disposed in (the control section 22 of) the endoscope apparatus 14. Furthermore, all components of the endoscope illumination apparatus 12 can be disposed in the endoscope apparatus 14.

The main body 16 further includes an input device 58, a system controller 60, and an image processing circuit 62. The image processing circuit 62 includes a variable amplification circuit (AMP) 64.

The input device 58 has a user interface having a function of enabling a power supply operation (ON/OFF) of the endoscope system 10, a setting of the observation mode, an adjustment of the quantity of the illumination light IL emitted from the endoscope illumination apparatus 12, and the like.

The system controller 60 controls the endoscope illumination apparatus 12, the imaging unit 30, and the image processing circuit 62 based on the information input to the input device 58. In addition, based on the operation determination result signal from the operation determination circuit 50, control of the quantity of light of the endoscope illumination apparatus 12 (primary light source 36) is performed. Details of the control by the system controller 60 will be described later. The system controller 60 may be configured as a system control circuit based on hardware or may be configured with a processor. In the case of configured by a processor, program code for causing the processor to function as the system controller 60 by the execution by the processor is stored in an external memory (not shown) accessible by the processor.

The image processing circuit 62 generates a image of an object by known image processing based on the imaging signal after the observation mode information input to the input device 58 and the imaging signal output from the imaging unit 30 as required are amplified by the AMP 64.

An image output device 18 displays the object image generated by the image processing circuit 62. For example, the image output device 18 is a monitor such as a liquid crystal display.

In addition, the primary light source 36 emits primary light. As the primary light, various kinds of light can be used depending on the light convertor 28. In the present embodiment, the primary light source 36 is a laser diode (LD) that emits blue laser light with an emission wavelength peak of 450 nm.

In order to drive the primary light source 36, the primary light source driver 38 supplies electric power to the primary light source 36 by a predetermined driving current or drive interval. In addition, the primary light source driver 38 receives a light source control signal from the system controller 60, and changes the driving of the primary light source 36 such as a driving current, a driving interval, and a suspension of the primary light source 36.

The optical coupler 40 includes an optical branching fiber coupler having two input ends and one output end. One input end of the optical branching fiber coupler is optically connected to the primary light source 36 by the optical connector (P1), and the other input end is optically connected to the detection light extractor 42 by the optical connector (P2). In addition, the output end of the optical branching fiber coupler is optically connected to the optical connector 32, which is the optical connector (P3), and as described above, the output end of the optical branching fiber coupler is optically connected to the light convertor 28 through the optical fiber 26. Therefore, the optical coupler 40 has the function of guiding the primary light from the primary light source 36 to the light convertor 28 through the optical fiber 26, and guiding part of the secondary light returning from the light convertor 28 through the optical fiber 26 to the detection light extractor 42.

Here, description will be made as to what part of the secondary light returning from the light convertor 28 is.

Figure 2:
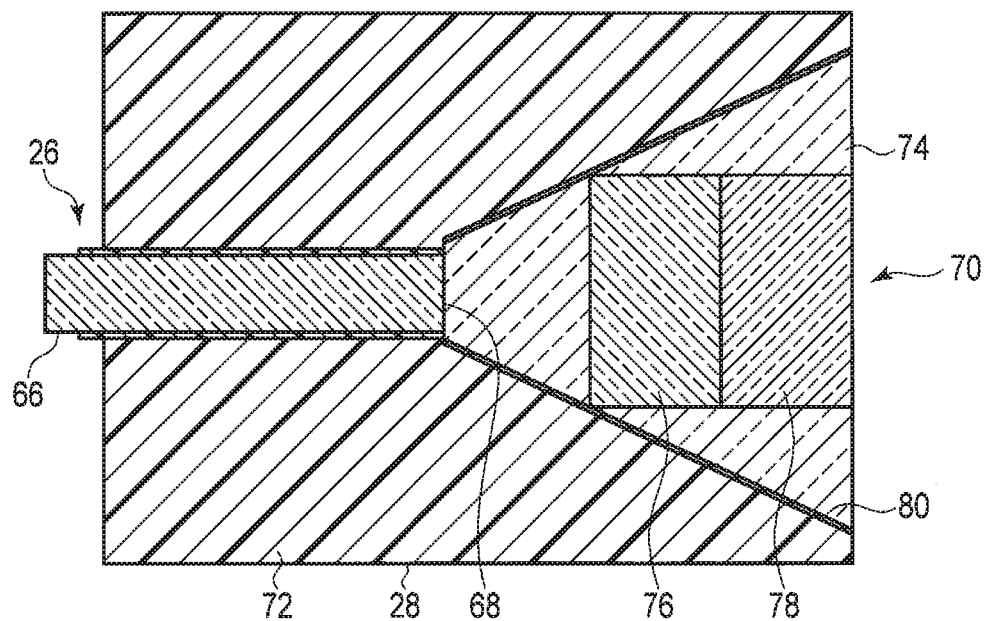
FIG. 2 is a cross-sectional view showing an example of a constitution of a light convertor.

The light convertor 28 is disposed in the vicinity of the tip end of the insertion section 20 and is fixed inside the insertion section 20 with an adhesive member or the like. As shown in FIG. 2, the light convertor 28 receives the primary light that is guided by the optical fiber 26 having a core 66 and is emitted from the exit end, which is the tip end portion thereof. That is, the exit end of the optical fiber 26 is an input part 68 of the light convertor 28. The light convertor 28 has a function of converting the primary light into secondary light having optical characteristics different from that of the primary light. Further, the light convertor 28 has a function of emitting part of the secondary light as the illumination light IL from an output part 70 toward an object O, and bringing another part of the secondary light as detection light to the exit end of the optical fiber 26.

Specifically, the light convertor 28 includes a holder 72, a light transmission member 74, a first light conversion member 76, a second light conversion member 78, and a reflection member 80.

The holder 72 has a cylindrical shape and holds the optical fiber 26 (the optical fiber exit end), the first and second light conversion members 76 and 78, and the light transmission member 74. Inside the holder 72, there are formed a fiber holding hole and a hollow portion of a truncated cone shape on the tip end side connected to the fiber holding hole. The diameter of the hollow portion gradually expands from the fiber holding hole toward the tip end face of the holder 72.

The reflection member 80 is formed to have a tapered surface that is the inner surface of the hollow portion of the holder 72. The reflection member 80 is a metal reflecting film obtained by thinly plating a metal such as silver or aluminum on the tapered surface of the hollow portion. When the primary light and the first light conversion light converted by the first light conversion member 76 enter it, the incident light is specularly reflected or diffusely reflected.

The light transmission member 74 is made of glass or silicone resin with high transmittance. The light transmission member 74 has a function of transmitting the primary light entering from the exit end of the optical fiber 26, and the wavelength-converted light emitted from the first light conversion member 76 into the input part 68 of the light convertor 28 that is the base end portion of the light transmission member 74.

The light transmission member 74 is disposed in the hollow portion. Specifically, the light transmission member 74 is disposed so as to surround the first and second light conversion members 76 and 78 that are both cylindrical in shape. That is, in the light convertor 28 (a hollow portion in the holder 72), the light transmission member 74, the first light conversion member 76, and the second light conversion member 78 are arranged in contact with each other in this order in the direction of emission of the primary light from the optical fiber exit end, which is the input part 68. The diameter of the first light conversion member 76 is the same as the diameter of the second light conversion member 78. The entire outer peripheral edge of the base end face of the first light conversion member 76 facing the input part 68 is in contact with the reflection member 80. The emission surface of the light transmission member 74, the emission surface of the second light conversion member 78, and the tip end face of the holder 72 are arranged on substantially the same plane. The emission surface of the light transmission member 74 and the emission surface of the second light conversion member 78 are the output part 70 of the light convertor 28.

The first light conversion member 76 and the second light conversion member 78 have such a laminated structure. Therefore, after being transmitted through the light transmission member 74, the primary light entering the light convertor 28 is emitted to the first light conversion member 76 and then the remaining primary light that has been transmitted through without being absorbed by the first light conversion member 76 is emitted to the second light conversion member 78.

Figure 3:
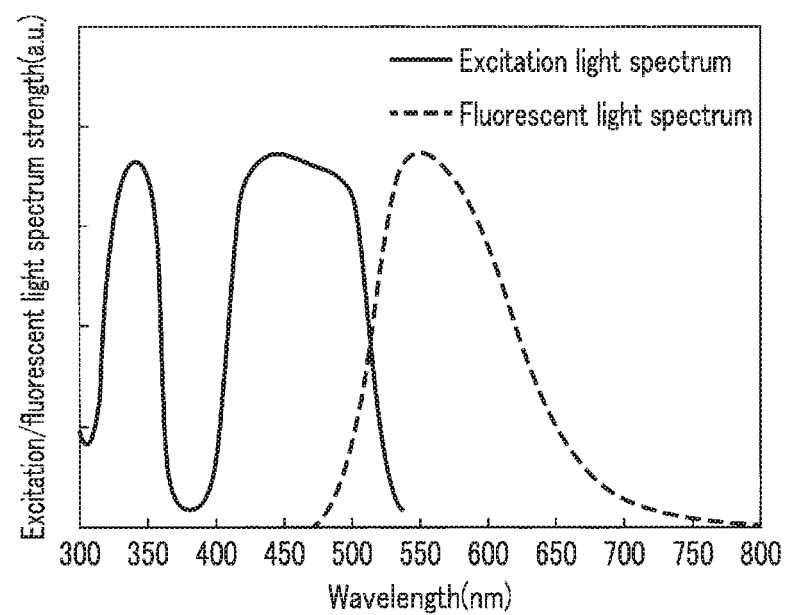
FIG. 3 is a diagram showing an example of optical characteristics of a first light conversion member in the light convertor.

The first light conversion member 76 has a first fluorescent substance functioning as a wavelength conversion member. The fluorescent substance has a property of absorbing the excitation light and generating fluorescent light, and this first fluorescent substance has fluorescent light spectrum as shown by the broken line with respect to the excitation light spectrum as indicated by the solid line in FIG. 3. Therefore, the first light conversion member 76 has properties of absorbing the primary light (blue laser light) emitted from the primary light source 36, and converting the wavelength into the first fluorescent light having a longer wavelength than the primary light. Specifically, the first fluorescent substance is a transparent ceramic fluorescent substance represented by YAG:Ce, which absorbs the primary light in the blue wavelength range and converts the wavelength into yellow fluorescent light. Therefore, the secondary light includes the first fluorescent light (yellow). In addition, the first light conversion member 76 (first fluorescent substance) has a property of transmitting the primary light that is not absorbed when it receives the primary light, without substantially widening its light distribution angle.

Figure 4:
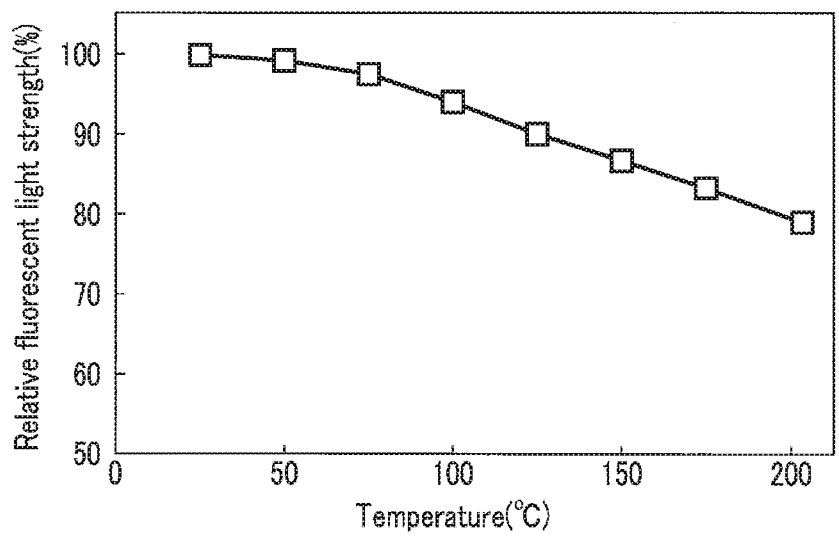
FIG. 4 is a diagram showing an example of temperature quenching characteristics of the first light conversion member.

Such a first light conversion member 76 (first fluorescent substance) has a temperature quenching characteristic in which the wavelength conversion efficiency decreases as the temperature at which the fluorescent substance is placed increases. Specifically, as shown in FIG. 4, first light conversion member 76 has characteristics in which the wavelength conversion efficiency of approximately 85% at 150° C. and approximately 80% at 200° C. is obtained when the room temperature is 25° C. as a reference. Temperature quenching represents reversible characteristic fluctuations such that it maintains the wavelength conversion efficiency when the temperature decreases (for example, approximately 100% at room temperature of 25° C.) after the wavelength conversion efficiency decreases (for example, approximately 85% at 150° C.) due to an increase in temperature).

The second light conversion member 78 has a diffusing member that is a scattering or reflection member for converting the incident primary light into diffusion light with widening divergence angle without changing their wavelength, and with reduced coherence. The diffusing member of the second light conversion member 78 has an optical property in which at least part of the incident primary light is emitted rearward (toward the first light conversion member 76) as diffusion light of the primary light. Specifically, the diffusing member is obtained by dispersing alumina diffusion particles having a refractive index higher than the refractive index of the sealing material in a transparent sealing material such as a silicone resin to cure the sealing material. When alumina particles having a particle size of several μm (refractive index 1.76) and silicone resin (refractive index 1.4) are used in combination, when alumina particles having a volume concentration of approximately 20% and a thickness of approximately 0.1 mm are used, it is possible to sufficiently widen the light distribution angle of the primary light in the light convertor 28 when primary light is received.

Figure 5:
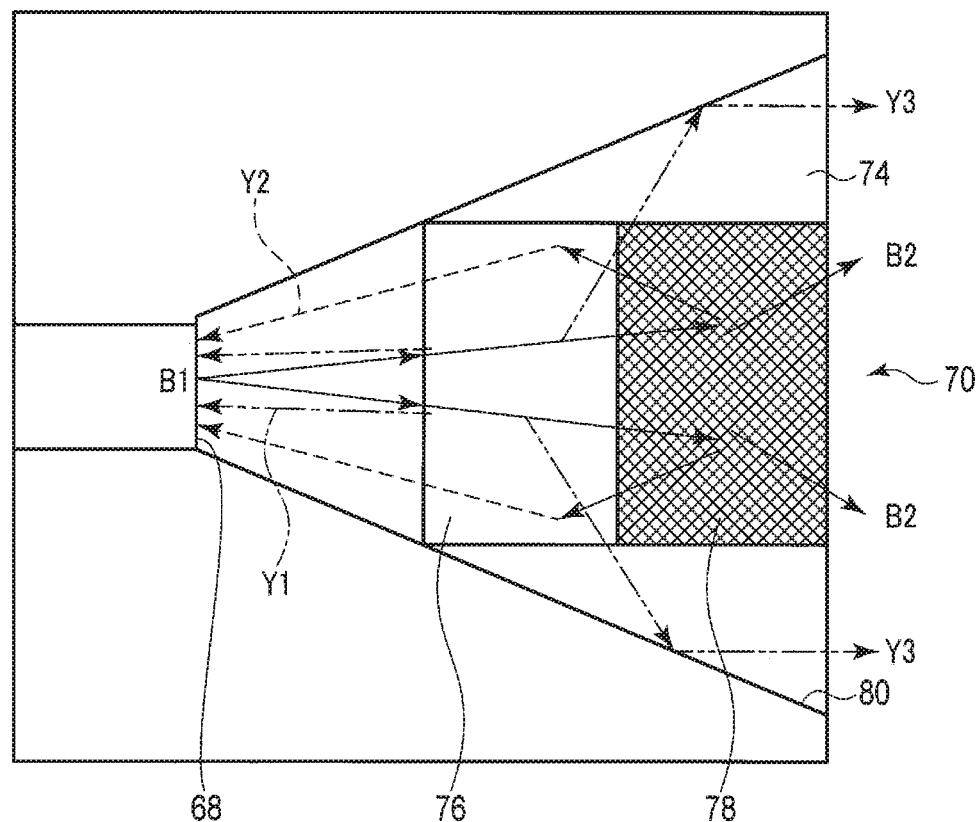
FIG. 5 is a diagram for explaining a direct irradiation type first light conversion light and an indirect irradiation type first light conversion light included in detection light.

In the light convertor 28 having such a constitution, as shown in FIG. 5, the primary light B1 emitted from the exit end of the optical fiber 26 and entering the input part 68 of the light convertor 28 is transmitted through the light transmission member 74, and is emitted to the first light conversion member 76. Part of the primary light B1 is absorbed by the first light conversion member 76 and wavelength-converted into the first fluorescent light (yellow), and anther part thereof is transmitted through the first light conversion member 76 and is emitted to the second light conversion member 78. In the present embodiment, in the first light conversion member 76, light that absorbs the primary light B1 not passing through the second light conversion member 78, and is light-converted is defined as direct irradiation type first light conversion light Y1. Therefore, the secondary light includes the direct irradiation type first light conversion light Y1.

On the other hand, the primary light B1 that is not absorbed by but transmitted through the first light conversion member 76 and emitted to the second light conversion member 78 is emitted to the second light conversion member 78. Then, by repeating scattering or reflection by diffusion particles (alumina) having a predetermined concentration arranged in the second light conversion member 78, the primary light B1 does not change the wavelength of the primary light B1 and is converted into diffusion primary light B2 having a wide light distribution angle by widening the light distribution angle of the primary light B1. In the present embodiment, the second light conversion light into which the primary light B1 is converted when the second light conversion member 78 is irradiated with the primary light B1 is defined as diffusion primary light B2. Therefore, the secondary light includes the diffusion primary light B2.

Part of the diffusion primary light B2 is emitted forward as the illumination light IL from the second light conversion member 78. In addition, another part is directly emitted from the second light conversion member 78 to the rearward first light conversion member 76 or emitted by at least one reflection by the reflection member 80 through the light transmission member 74. Part of the diffusion primary light B2 with which the first light conversion member 76 is irradiated is absorbed by the first light conversion member 76 and wavelength-converted into the first fluorescent light (yellow). In addition, another part of the diffusion primary light B2 with which the first light conversion member 76 is irradiated is transmitted through the first light conversion member 76, and the reflection member 80 is irradiated with another part of the diffusion primary light B2 through the light transmission member 74, and another part of the diffusion primary light B2 is reflected by the reflection member 80 at least once, enters the first light conversion member 76 again through the light transmission member 74, and is wavelength-converted. In the present embodiment, in the first light conversion member 76, light that absorbs part of the second light conversion light (diffusion primary light B2) converted through the second light conversion member 78 as described above, and is light-converted is defined as indirect irradiation type first light conversion light Y2. Therefore, the secondary light includes the indirect irradiation type first light conversion light Y2.

When the second light conversion member 78 is detached from the light transmission member 74 or the first light conversion member 76, for example, the emission surface of the first light conversion member 76 comes in contact with air. In this case, on the emission surface of the first light conversion member 76, the return light of the primary light is generated due to the Fresnel reflection to the air. The quantity of the diffusion primary light B2 emitted from the second light conversion member 78 in the case where it is not detached is larger than the quantity of the return light of the primary light due to such Fresnel reflection.

The direct irradiation type first light conversion light Y1 and the indirect irradiation type first light conversion light Y2 are the first fluorescent light that is isotropically emitted without directivity at the time of light conversion. Part Y3 of this first fluorescent light is reflected at least once through the second light conversion member 78 and/or by the reflection member 80, and is emitted as illumination light IL forward from the output part 70. Further, another part of the first fluorescent light is emitted to the optical fiber 26 from the exit end of the optical fiber 26 toward the input part 68 of the light convertor 28. The first fluorescent light entering the optical fiber 26 is guided to the operation determination circuit 50 (detection light extractor 42) through the optical fiber 26, the optical coupler 40, and the like.

As described above, when the light convertor 28 having the first and second light conversion members 76 and 78 is irradiated with the primary light B1 from the exit end of the optical fiber 26, as the detection light, part of the direct irradiation type and the indirect irradiation type first light conversion light Y1 and Y2 enter the optical fiber 26. In this case, the direct irradiation type first light conversion light Y1 occupies a greater proportion of the detection light than the indirect irradiation type first light conversion light Y2.

The detection light extractor 42 is a detector that receives the detection light emitted from the light convertor 28 through the optical fiber 26 and the optical coupler 40, and outputs a detection light output signal corresponding to the quantity of the detection light. That is, the detection light extractor 42 detects the detection light in real time, and has a function of outputting a detection light output signal corresponding to the detected light quantity to the operation determination circuit 50. Specifically, the detection light extractor 42 includes a light quantity sensor (photodiode) that outputs an electric signal with respect to the quantity of light received in the visible light range entering the light receiving surface. This light quantity sensor is a light receiving element having a characteristic in which the sensitivity is higher in the wavelength range of the first fluorescent light than in the wavelength range of the blue laser light that is the primary light. Furthermore, the detection light extractor 42 has an amplifier circuit that amplifies the electric signal output from the light quantity sensor. The amplified electrical signal is output to the operation determination circuit 50 as a detection light output signal.

The primary light source drive monitor 44 acquires from the primary light source driver 38 the primary light source drive information that is the drive information of the primary light source 36 necessary for setting the standard detection light range used for determining the operation of the first and second light conversion members 76 and 78. The primary light source drive information is, for example, a drive current value driving the blue LD of the primary light source 36, and the primary light source drive monitor 44 has a function of outputting the drive current value information to the operation determination circuit 50. The standard detection light range will be described later.

The standard detection light information storage 46 is a memory that records in advance an information table indicating the correlation between the value of the quantity of the primary light emitted from the primary light source 36 with respect to the primary light source drive information and the value of the detection light output signal output from the detection light extractor 42. Specifically, the standard detection light information storage 46 records the correlation between at least one of a drive current, a drive pulse (drive interval), or an drive voltage at which the primary light source driver 38 drives the primary light source 36, and a setting value of the quantity of the primary light set by the system controller 60, and the detection light output signal value corresponding to the quantity of the detection light detected by the detection light extractor 42.

The detection light information temporary memory 48 is a memory that temporarily records the detection light output signal value, the operation estimation result, and the like at the time of operation estimation by the operation determination circuit 50 (operation estimation circuit 52) described later.

Based on the amount of change in the detection light output signal output from the detection light extractor 42 by the operation estimation circuit 52, the abnormal operation determination circuit 54, and the abnormal operation member identification circuit 56, the operation determination circuit 50 determines the operation of the first and second light conversion members 76 and 78. It should be noted that all or part of the operation determination circuit 50 may be configured as an operation determination circuit by hardware or may be configured with a processor. In other words, all or part of the operation estimation circuit 52, the abnormal operation determination circuit 54, and the abnormal operation member identification circuit 56 may be configured as a hardware operation estimation circuit, an abnormal operation determination circuit, an abnormal operation member identification circuit, etc., or may be configured by a processor. In the case where the operation determination circuit 50 (the operation estimation circuit 52, the abnormal operation determination circuit 54, and the abnormal operation member identification circuit 56) is configured by a processor, program code for causing the processor to function as the operation determination circuit 50 (the operation estimation circuit 52, the abnormal operation determination circuit 54, and the abnormal operation member identification circuit 56 by the execution by the processor is stored in an external memory (not shown) accessible by the processor.

Based on the primary light source drive information acquired by the primary light source drive monitor 44, the operation determination circuit 50 calculates the detection light quantity standard value with reference to the information table stored in the standard detection light information storage 46. Here, the detection light quantity is a value obtained by calculating the value of the detection light output signal output from the detection light extractor 42 as a ratio (calibration) with respect to the output signal value of the primary light corresponding to the quantity of the primary light emitted from the primary light source 36 indicated by the primary light source drive information output from the primary light source drive monitor 44 in accordance with the quantity of the detection light emitted from the light convertor 28 and entering the detection light extractor 42. This is formulated by detection light quantity=detection light output signal value/primary light output signal value. In this way, in the operation determination circuit 50, the value of the detection light output signal is normalized based on the primary light source drive information for use. Therefore, the detection light quantity standard value is also a value normalized based on the primary light source drive information.

Figure 6:
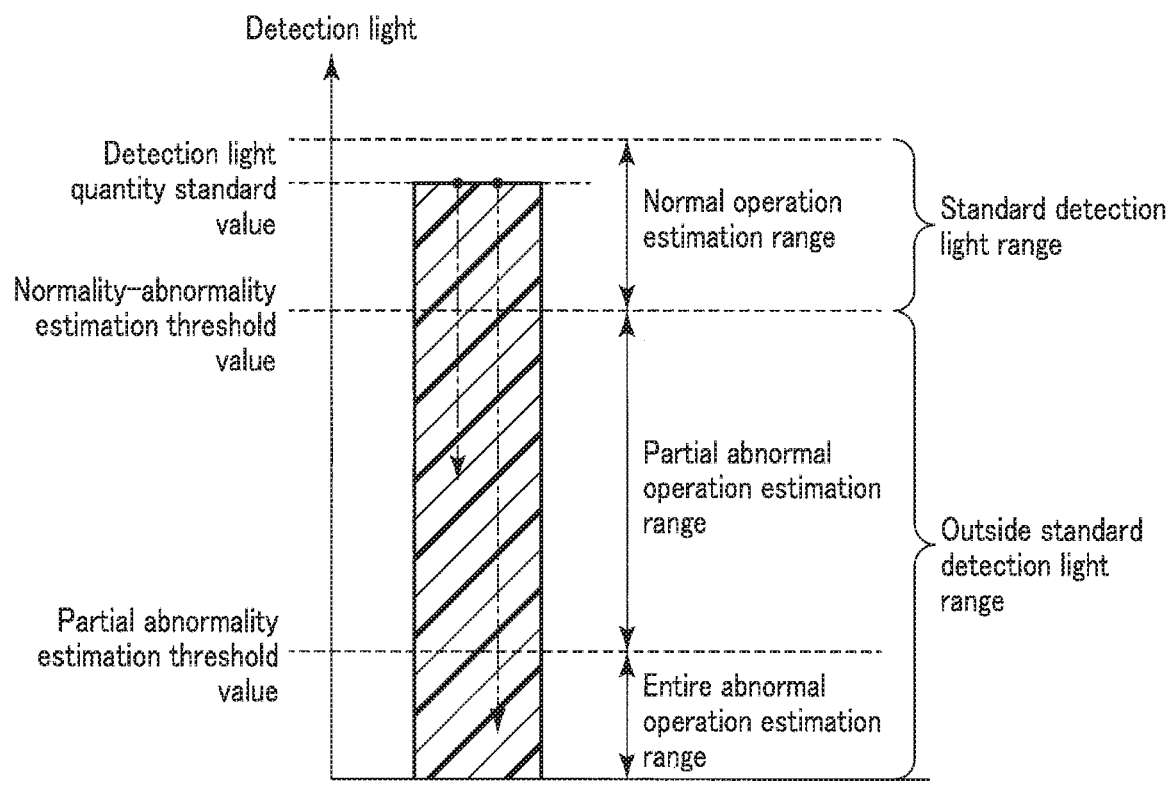
FIG. 6 is a diagram for explaining a detection light quantity standard value, a normal operation estimation range, a partial abnormal operation estimation range, and an entire abnormal operation estimation range.

Then, as shown in FIG. 6, the operation determination circuit 50 sets a standard detection light range including the detection light quantity standard value. The lower limit detection light quantity value of this standard detection light range is a normality-abnormality estimation threshold value. Further, the operation determination circuit 50 sets a predetermined detection light quantity value for dividing a range outside the set standard detection light range into two abnormality detection ranges, namely first and second abnormality detection ranges, as a boundary line (partial abnormality estimation threshold value). That is, the operation determination circuit 50 sets, as the first abnormality detection range, that is, the partial abnormal operation estimation range, a portion having a small difference from the standard detection light range out of the divided standard detection light range, and sets, as the second abnormality detection range, that is, the entire abnormal operation estimation range, a portion having a larger difference from the standard detection light range.

The operation estimation circuit 52 estimates the current operation of the current first and the second light conversion member 76 and 78 (in real time) by comparing the detection light of the first fluorescent light with the above-described three ranges. Specifically, when the normalized detection light output signal value is within the standard detection light range, it is estimated to be a normal operation, and when the normalized detection light output signal value is outside the standard detection light range and is equal to or greater than the partial abnormality estimation threshold value, it is estimated to be a partial abnormal operation, and when the normalized detection light output signal value is smaller than the partial abnormality estimation threshold value outside the standard detection light range, it is estimated to be an entire abnormal operation.

The operation determination circuit 50 sends an operation determination result signal corresponding to the operation estimation result by the operation estimation circuit 52 to the system controller 60. Specifically, when the operation estimation circuit 52 estimates that the operation is the partial abnormal operation or the entire abnormal operation, the operation determination circuit 50 sends as an operation determination result signal a signal for switching an output to operation verification primary light that is a low light quantity with respect to the quantity of the primary light emitted from the current primary light source 36. It should be noted that the operation verification primary light when the operation estimation circuit 52 estimates that the operation is the entire abnormal operation is set to a lower light quantity than the operation verification primary light when the operation estimation circuit 52 estimates that the operation is the partial abnormal operation.

Further, the operation determination circuit 50 records the normalized detection light output signal value and operation estimation result at the time of estimation by the operation estimation circuit 52 in the detection light information temporary memory 48.

The abnormal operation determination circuit 54 determines whether the first and second light conversion members 76 and 78 are in an abnormal operation by comparing the verification detection light output signal value output from the detection light extractor 42 with the above-described three operation estimation ranges with respect to the verification detection light returning from the light convertor 28 when the operation verification primary light enters the light convertor 28.

In this case, the verification detection light output signal value is also normalized with respect to the output signal value of the operation verification primary light for use, as in the detection light output signal value. Therefore, the above-described three operation estimation ranges, that is, the standard detection light range, which is identical to the normal operation estimation range, the partial abnormal operation estimation range, and the entire abnormal operation estimation range can be used as they are without resetting. Therefore, the abnormal operation determination circuit 54 determines the entire abnormal operation or the partial abnormal operation depending on which range the normalized verification detection light output signal value exists in of the partial abnormal operation estimation range and the entire abnormal operation estimation range.

It should be noted that the operation determination circuit 50 has a function of comparing an abnormal operation determination result, which is a result of comparing a normalized verification detection light output signal value by the abnormal operation determination circuit 54 with the three operation estimation ranges, with the previous operation estimation result by the operation estimation circuit 52. When the operation estimation result and the abnormal operation determination result are the same, the operation determination circuit 50 validates the operation estimation result by the operation estimation circuit 52. On the other hand, when the operation estimation result and the abnormal operation determination result are different, the operation determination circuit 50 selects the abnormal operation determination result by the abnormal operation determination circuit 54.

The abnormal operation member identification circuit 56 identifies an operation abnormality of either one or both of the first and second light conversion members 76 and 78 based on an amount of difference between the normalized detection light output signal value for the primary light estimated to be an abnormal operation by the operation estimation circuit 52 and the normalized verification detection light output signal value for the operation verification primary light.

It should be noted that, although not shown in the drawing, the operation determination circuit 50 records the relations between the fluctuation direction and the amount of fluctuation of the verification detection light output signal value, and a detection light output signal value of the operation estimation circuit 52 when an operation abnormality occurs by the first and second light conversion members 76 and 78. Therefore, the abnormal operation member identification circuit 56 can identify the member that has caused the abnormal operation by a difference between the normalized detection light output signal value of the operation estimation result by the operation estimation circuit 52 and the normalized verification detection light output signal value.

Specifically, for example, when the normalized verification detection light output signal value increases with respect to the normalized detection light output signal value estimated to be a partial abnormal operation, and the verification detection output signal value reaches the standard detection light range, it is identified that the first light conversion member 76 is in an abnormal operation (temperature quenching).

In addition, when the normalized verification detection light output signal value hardly changes with respect to the normalized detection light output signal value estimated to be a partial abnormal operation, and both are in partial abnormality estimation range, it is identified that the first light conversion member 76 is not in an abnormal operation but the second light conversion member 78 is in an abnormal operation (detachment).

In addition, when the normalized verification detection light output signal value hardly changes with respect to the normalized detection light output signal value estimated to be the entire abnormal operation, and both are in the entire abnormality estimation range, it is identified that the first and second light conversion members 76 and 78 are in a abnormal operation (burning of the first fluorescent substance, detachment of the first and second light conversion members 76 and 78), where neither does not function.

In this manner, the abnormal operation member identification circuit 56 identifies the type of abnormal operation of the first and second light conversion members 76 and 78 in the light convertor 28.

As described above, the system controller 60 receives the operation determination result signal output from the operation determination circuit 50, and has a function of controlling the primary light source driver 38, the imaging unit 30, the image processing circuit 62, and the like. Specifically, the system controller 60 has a function of performing the following control when receiving a signal of the partial abnormality or entire abnormality estimation results from the operation estimation circuit 52 as the operation determination result signal.

The system controller 60 outputs a control signal for outputting predetermined (low quantity of light) operation verification primary light for a necessary for the abnormal operation determination circuit 54 to the primary light source driver 38.

(Preferably) The system controller 60 outputs to the image processing circuit 62 a control signal for assigning the amount of difference between the quantity of the operation verification primary light and the quantity of the primary light to the increase amount for amplifying the imaging signal by the AMP 64.

(Preferably) The system controller 60 outputs to the imaging unit 30 and the image processing circuit 62 a control signal for lowering the frame rate and outputting the operation verification primary light within the non-exposure period of the imaging unit 30.

(Preferably) An amplification circuit is provided in the operation determination circuit 50, and the system controller 60 outputs to the operation determination circuit 50 a control signal for assigning the amount of difference between the quantity of the operation verification primary light and the quantity of the primary light to the increase amount for amplifying the detected detection light output signal (electric signal) output from the detection light extractor 42.

The system controller 60 outputs such a control signal to control each corresponding part, whereby when the operation determination circuit 50 shifts from the operation estimation circuit 52 to the abnormal operation determination circuit 54, image acquisition can be continuously implemented.

Hereinafter, the operation of the endoscope system 10 configured as described above will be described.

First, the user selects a predetermined observation mode of the endoscope apparatus 14 and inputs the selected observation mode to the input device 58. The predetermined mode information input from the input device 58 is transmitted to the system controller 60. The system controller 60 uses the control information corresponding to the selected observation mode to perform control of the endoscope illumination apparatus 12, the imaging unit 30 and the image processing circuit 62.

That is, the system controller 60 outputs a control signal to the primary light source driver 38, and the primary light source driver 38 controls the primary light source 36. The primary light source 36 emits a primary light (blue laser light), and the emitted primary light is guided by the optical coupler 40 and the optical fiber 26, and enters the input part 68 of the light convertor 28. In addition, the primary light source drive monitor 44 acquires From the primary light source driver 38 the primary light source drive information that is the drive information of the primary light source 36 necessary for setting the standard detection light range used for determining the operation of the first and second light conversion members 76 and 78.

The light convertor 28 converts the primary light entering the light convertor 28 into secondary light including the direct irradiation type first light conversion light Y1 and the indirect irradiation type first light conversion light Y2, and the primary light that has not been light-converted. Then, the light convertor 28 emits part of the secondary light as the illumination light IL from the output part 70 toward the object O, and also emits another part of the secondary light (part of the direct irradiation type first light conversion light Y1 and the indirect irradiation type first light conversion light Y2) as detection light from the input part 68. The detection light entering the input part 68 is guided by the optical fiber 26 and the optical coupler 40, and enters the detection light extractor 42.

The detection light extractor 42 outputs the detection light output signal corresponding to the quantity of the received detection light by the photodiode and the amplification circuit to the operation determination circuit 50. The operation determination circuit 50 determines the operation of the first and second light conversion members 76 and 78 based on the change amount of the detection light output signal output from the detection light extractor 42.

Figure 7:
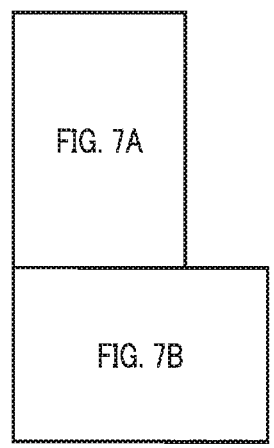
FIG. 7 is a diagram showing the relation between FIG. 7A and FIG. 7B.
Figure 7A:
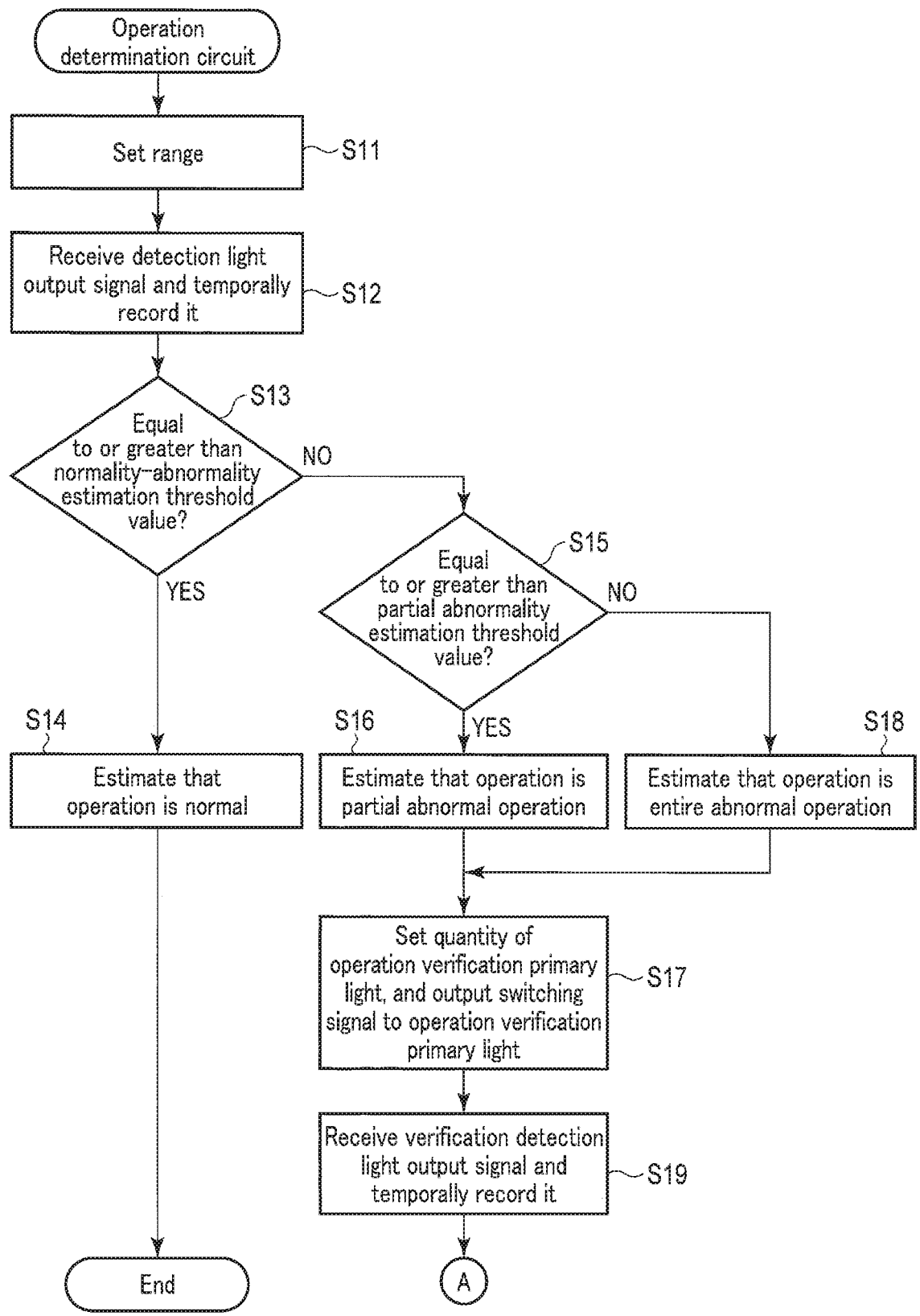
FIG. 7A is a diagram showing part of a flowchart for explaining the operation of an operation determination circuit.

Hereinafter, the operation of the operation determination circuit 50 will be described based on a series of flowcharts shown in FIG. 7A and FIG. 7B divided as shown in FIG. 7.

Upon starting the operation, the operation determination circuit 50 first sets the standard detection light range, the partial abnormal operation estimation range, and the entire abnormal operation estimation range (step S11). That is, based on the primary light source drive information acquired by the primary light source drive monitor 44, the detection light quantity standard value is calculated with reference to a information table stored in the standard detection light information storage 46, and the above three ranges are set based on the detection light quantity standard value.

Next, the operation determination circuit 50 receives the detection light output signal output from the detection light extractor 42, normalizes it based on the primary light source drive information acquired by the primary light source drive monitor 44, and records the normalized signal in the detection light information temporary memory 48 (step S12).

Then, the operation estimation circuit 52 of the operation determination circuit 50 determines in real time whether the normalized detection light output signal value is equal to or greater than the normality-abnormality estimation threshold value, that is, whether it is within the standard detection light range (Step S13). Here, when it is determined that the normalized detection light output signal value is equal to or greater than the normality-abnormality estimation threshold value, the operation estimation circuit 52 estimates that the operation is normal (step S14), and the operation determination circuit 50 estimates end the operation. Then, at the next operation timing, the operation from step S11 is repeated.

Figure 8:
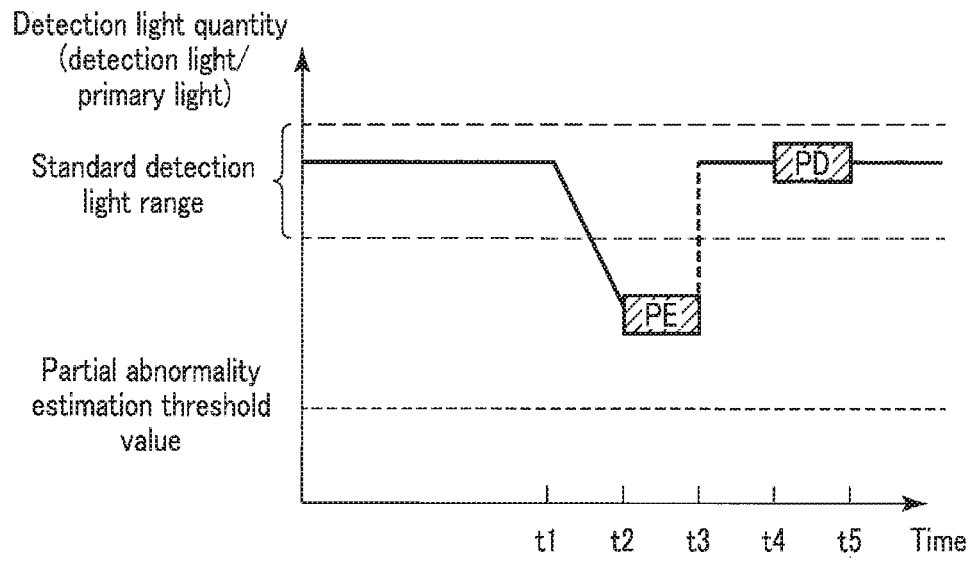
FIG. 8 is a diagram showing a transition of the detection light quantity amount in the case where the abnormal operation is temperature quenching of the first light conversion member.

For example, until the time t1 in FIG. 8, the detection light quantity that is the normalized detection light output signal is operating within the standard detection light range. Therefore, any abnormality does not occur to the light convertor 28, and there is no need to change the quantity of the primary light generated by the primary light source 36 from the quantity of light corresponding to the observation mode selected by the user to another quantity of light. In such a case, the operation estimation circuit 52 estimates that the operation is normal, and does not transmit an operation determination signal for changing the quantity of the primary light from the operation determination circuit 50 to the system controller 60.

In addition, in the above-described step S14, the estimation result in which the operation is normal and the information about the three ranges set in the above step S11 may be recorded in the detection light information temporary memory 48. By doing so, when the estimation result indicating that the operation is normal is recorded in the detection light information temporary memory 48 at the next operation of the operation determination circuit 50, in step S11, it is possible to set the three ranges from the information recorded in the detection light information temporary memory 48 without calculating the detection light quantity standard value based on the primary light source drive information.

On the other hand, when it is determined in step S13 that the normalized detection light output signal value is not equal to or greater than the normality-abnormality estimation threshold value, the operation estimation circuit 52 determines whether the normalized detection light output signal value is equal to or greater than partial abnormality estimation threshold value that is outside of the standard detection light range, that is whether it is within the partial abnormal operation estimation range (step S15). Here, when it is determined that the normalized detection light output signal value is equal to or greater than the partial abnormality estimation threshold value, the operation estimation circuit 52 estimates that the operation is a partial abnormal operation and records the estimation result in the detection light information temporary memory 48 (step S16).

Then, the operation determination circuit 50 sets the quantity of the operation verification primary light, and transmits to the system controller 60 a switching signal to the operation verification primary light with the quantity of light (step S17). In other words, in this case, since the estimation result by the operation estimation circuit 52 shows a partial abnormal operation, the operation determination signal that is the partial abnormal operation estimation identification signal is transmitted to the system controller 60 as a switching signal for changing the quantity of the primary light generated by the primary light source 36 into the quantity of the operation verification primary light smaller than the quantity of light corresponding to the observation mode.

When it is determined in step S15 that the normalized detection light output signal value is smaller than the partial abnormality estimation threshold value, the operation estimation circuit 52 estimates that the operation is the entire abnormal operation, and records the estimation result in the detection light information temporary memory 48 (step S18).

Then, the operation determination circuit 50 sets the quantity of the operation verification primary light, and transmits to the system controller 60 a switching signal to the operation verification primary light with the quantity of light (step S17). In other words, in this case, since the estimation result by the operation estimation circuit 52 shows an entire abnormal operation, the operation determination signal that is the entire abnormal operation estimation identification signal is transmitted to the system controller 60 as a switching signal for changing the quantity of the primary light generated by the primary light source 36 into the quantity of the operation verification primary light smaller than the quantity of light when estimated to be partially abnormal.

The system controller 60 outputs to the primary light source driver 38 a control signal for switching to the operation verification primary light by the operation determination signal that is the partial abnormal operation estimation identification signal or the entire abnormal operation estimation identification signal, and the primary light source driver 38 controls the quantity of light of the primary light source 36 so that the primary light emitted from the primary light source 36 becomes the operation verification primary light. The primary light source drive monitor 44 acquires the primary light source drive information that is drive information of the primary light source 36 at this time from the primary light source driver 38. In addition, since operation verification primary light is emitted from the primary light source 36, verification detection light emitted from the light convertor 28 enters the detection light extractor 42. The detection light extractor 42 outputs a verification detection light output signal corresponding to the quantity of the verification detection light to the operation determination circuit 50.

Therefore, the operation determination circuit 50 receives the verification detection light output signal output from the detection light extractor 42, normalizes it based on the primary light source drive information acquired by the primary light source drive monitor 44, and records the normalized signal in the detection light information temporary memory 48 (step S19).

For example, during the period from time t1 to time t2 in FIG. 8, the detection light quantity that is the normalized detection light output signal value is changed to a range outside the standard detection light range and larger than the partial abnormality estimation threshold value. Therefore, during the abnormal operation estimation period PE that is a period from the time t2 to the time t3, the operation estimation circuit 52 estimates that the light convertor 28 is in an abnormal operation, and the primary light emitted by the primary light source 36 is switched to verification primary light. Then, during the abnormal operation determination period PD, which is the period from the time t4 to the time t5 after the lapse of the predetermined time from the time t3, the abnormal operation determination by the abnormal operation determination circuit 54 is performed.

That is, the abnormal operation determination circuit 54 of the operation determination circuit 50 determines whether the normalized verification detection light output signal value is equal to or greater than the normality-abnormality estimation threshold value, that is, whether it is within the standard detection light range (Step S20). Here, when it is determined that the normalized verification detection light output signal value is equal to or greater than the normality-abnormality estimation threshold value, the abnormal operation determination circuit 54 determines that the operation is normal (step S21). In this way, when the determination results are different such that the estimation result by the operation estimation circuit 52 shows an abnormal operation, and the abnormal operation determination result by the abnormal operation determination circuit 54 shows a normal operation, the operation determination circuit 50 selects the determination result by the abnormal operation determination circuit 54 to determine it as the determination result. Then, the operation determination circuit 50 sets the quantity of the primary light and transmits to the system controller 60 a switching signal to the primary light of the quantity of light (step S22). That is, in this case, since the determination result shows a normal operation, an operation determination signal that is a normal operation identification signal is transmitted to the system controller 60 as switching signal for returning the quantity of the primary light generated by the primary light source 36 into the quantity of the primary light corresponding to the original observation mode from the quantity of the operation verification primary light. Then, the operation determination circuit 50 ends the operation, and repeats the operations from the step S11 at the next operation timing.

In addition, the results where the estimation result by the operation estimation circuit 52 shows an abnormal operation and the abnormal operation determination result by the abnormal operation determination circuit 54 shows a normal operation indicates that the verification detection light output signal value has increased by a predetermined amount from the detection light output signal value. Therefore, in this case, the operation determination circuit 50 determines that the operation is normal, and (although not shown) also determines that the result by the operation estimation circuit immediately before the determination with respect to the abnormal operation is the temperature quenching of the first light conversion member 76.

In the example of FIG. 8, during the abnormal operation determination period PD, which is the period from the time t4 to the time t5, the abnormal operation determination circuit 54 determines that the operation is normal, and accordingly the operation determination circuit 50 determines that the light convertor 28 is in a normal operation. Therefore, the primary light source 36 is switched so as to emit the primary light according to the observation mode.

On the other hand, when it is determined in step S20 that the normalized verification detection light output signal value is not equal to or greater than the normality-abnormality estimation threshold value, the abnormal operation determination circuit 54 determines whether the normalized verification detection light output signal value is equal to or greater than the partial abnormality estimation threshold value that is outside the standard detection light range, that is, whether it is within the partial abnormal operation estimation range (step S23). Here, when it is determined that the normalized verification detection light output signal value is equal to or greater than the partial abnormality estimation threshold value, the abnormal operation determination circuit 54 determines that the operation is a partial abnormal operation (step S24).

As described above, when the abnormal operation determination circuit 54 determines that the operation is a partial abnormal operation, the abnormal operation member identification circuit 56 of the operation determination circuit 50 identifies that member performs an abnormal operation of the first and second light conversion members 76 and 78 based on an amount of difference between the normalized detection light output signal value and the normalized verification detection light output signal value. Specifically, based on the change rate of the verification detection light output signal value with respect to the normalized detection light output signal value, the abnormal operation member identification circuit 56 identifies the type of abnormal operation of the first and second light conversion members 76 and 78 in the light convertor 28.

That is, the abnormal operation member identification circuit 56 determines whether the normalized verification detection light output signal value has increased more than the predetermined amount with respect to the normalized detection light output signal value recorded in the detection light information temporary memory 48 (step S25). Here, when it is determined that the normalized verification detection light output signal value has increased more than the predetermined amount with respect to the normalized detection light output signal value, the abnormal operation member identification circuit 56 determines that the abnormal operation type is the abnormal operation of the first light conversion member 76, that is, temperature quenching of the first fluorescent substance (step S26). Then, the operation determination circuit 50 sets the quantity of the primary light and transmits to the system controller 60 a switching signal to the primary light of the quantity of light (step S22). That is, when the abnormal operation member identification circuit 56 identifies that the abnormal operation type is the temperature quenching of the first fluorescent substance, the operation determination circuit 50 transmits an operation determination signal that is the first light conversion member abnormal operation identification signal to the system controller 60 as a switching signal for causing the quantity of the primary light generated by primary light source 36 to be larger than that of the operation verification primary light. For example, when receiving the first light conversion member abnormal operation identification signal as an operation determination signal, the system controller 60 performs control such that primary light whose quantity is larger than a quantity of the operation verification primary light and is smaller than a quantity of light in accordance with the observing mode is emitted from the primary light source 36. The control may be performed, for example, during a predetermined period of time during which the temperature quenching is canceled due to the lowering of the temperature of the first fluorescent substance, and after the lapse of the predetermined time, the primary light of the quantity of light corresponding to the observation mode may be emitted. Then, the operation determination circuit 50 ends the operation, and repeats the operations from the step S11 at the next operation timing.

On the other hand, when it is determined in step S25 that the normalized verification detection light output signal value has not increased more than the predetermined amount with respect to the normalized detection light output signal value, that is, when it is determined that the normalized verification detection light output signal value and the normalized detection light output signal value recorded in the detection light information temporary memory 48 are substantially equal to each other, the abnormal operation member identification circuit 56 determines whether a difference between both of, the larger one of, or the smaller one of the normalized verification detection light output signal value and the detection light output signal value, and the standard detection light range is smaller than a predetermined amount (Step S27). Here, in the partial abnormality determination, the difference from the standard detection light range is smaller than the predetermined amount. Therefore, when it is determined that the difference from the standard detection light range is smaller than the predetermined amount, the abnormal operation member identification circuit 56 determines that the type of abnormal operation is an abnormal operation (detachment) of the second light conversion member (Step S28).

Figure 9:
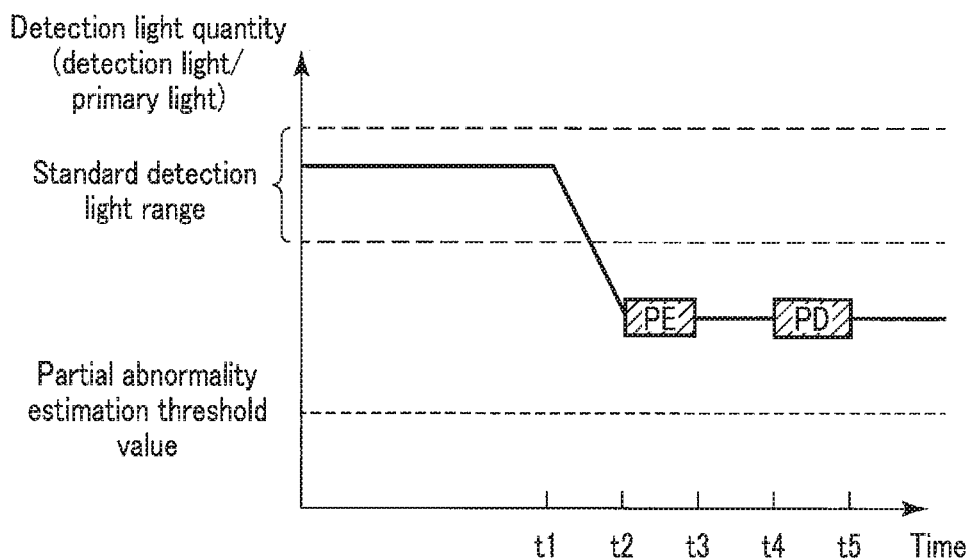
FIG. 9 is a diagram showing a transition of the detection light quantity in the case where the abnormal operation is an abnormal operation of the second light conversion member.

For example, in the example of FIG. 9, as in the example of FIG. 8, the operation estimation circuit 52 estimates that the light convertor 28 is in an abnormal operation during the abnormal operation estimation period PE that is the period from time t2 to t3, and the primary light emitted by the primary light source 36 is switched to the verification primary light of partial abnormal operation. Then, during abnormal operation determination period PD, which is a period from time t4 to time t5, when the abnormal operation determination circuit 54 performs abnormal operation determination, the normalized verification detection light output signal value by the operation verification primary light continues to be in an range larger than the partial abnormal operation estimation threshold value of the partial abnormal operation estimation range, whereby it is identified that the operation is a partial abnormal operation.

Then, the operation determination circuit 50 sets the quantity of the primary light and transmits to the system controller 60 a switching signal to the primary light of the quantity of light (step S22). That is, when the abnormal operation member identification circuit 56 identifies that the second light conversion member 78 is in an abnormal operation, the operation determination circuit 50 sends to the system controller 60 an operation determination signal that is the second light conversion member abnormal operation identification signal as a switching signal for causing the quantity of the primary light generated by the primary light source 36 to be equal to or smaller than that of the operation verification primary light of the partial abnormal operation. For example, when receiving the second light conversion member abnormal operation identification signal as the operation determination signal, the system controller 60 performs control such that the primary light of the quantity of light that is smaller than the quantity of the operation verification primary light of the partial abnormal operation is emitted from the primary light source 36. Then, the operation determination circuit 50 ends the operation, and repeats the operations from the step S11 at the next operation timing.

When it is determined in step S24 that the operation is a partial abnormal operation, since it is not entire abnormal operation, the determination in step S27 may be skipped, and the process may proceed from step S25 to step S28.

In addition, when it is determined in step S23 that the normalized verification detection light output signal value normalized is smaller than the partial abnormality estimation threshold value, the abnormal operation determination circuit 54 determines that the operation is an entire abnormal operation (step S29). Then, the normalized verification detection light output signal value and the normalized detection light output signal value recorded in the detection light information temporary memory 48 are in the entire abnormal operation estimation range, that is, they are substantially equal to each other, whereby the abnormal operation member identification circuit 56 determines whether a difference between both of, the larger one of, or the smaller one of the normalized verification detection light output signal value and the detection light output signal value, and the standard detection light range is smaller than a predetermined amount (Step S27). Here, at the time of the overall abnormality determination, the difference from the standard detection light range is equal to or greater than the predetermined amount. Therefore, when it is determined that the difference from the standard detection light range is not smaller than the predetermined amount, the abnormal operation member identification circuit 56 identifies that the type of abnormal operation is an abnormal operation (burning of the first fluorescent substance, detachment of the first and second light conversion members 76 and 78) in which the first and second light conversion members 76 and 78 do not function (step S30). Then, the operation determination circuit 50 sets the quantity of the primary light and transmits to the system controller 60 a switching signal to the primary light of the quantity of light (step S22). That is, when the abnormal operation member identification circuit 56 identifies that the first and second light conversion members 76 and 78 operate abnormally, the operation determination circuit 50 sends to the system controller 60 an operation determination signal that is the first and second light conversion member abnormal operation identification signal as a switching signal for causing the quantity of the primary light generated by the primary light source 36 to be equal to or smaller than that of the operation verification primary light of the entire abnormal operation. For example, when receiving the first and the second light conversion member abnormal operation identification signal as the operation determination signal, the system controller 60 performs control such that the primary light of the quantity of light that is smaller than the quantity of the operation verification primary light of the entire abnormal operation is emitted from the primary light source 36. Then, the operation determination circuit 50 ends the operation, and repeats the operations from the step S11 at the next operation timing.

When it is determined in step S29 that the operation is entire abnormal operation, since it is not a partial abnormal operation, the determination in step S27 may be skipped, and the process may proceed from step S29 to step S30.

As described above, the endoscope illumination apparatus 12 according to the first embodiment includes a primary light source 36 that emits primary light, a light convertor 28 that converts the primary light emitted from the primary light source 36 into secondary light having optical characteristics different from that of the primary light, and emits at least part of the secondary light as detection light and illumination light IL a detection light extractor 42 that receives the detection light, and outputs a detection light output signal corresponding to the quantity of the detection light, and an operation determination circuit 50 that determines the operation of the light convertor 28. Here, the light convertor 28 includes the first and second light conversion members 76 and 78 that receive the primary light and convert at least one of the optical properties of the primary light, and an input part 68 that the primary light enters. The detection light includes at least one of direct irradiation type first light conversion light Y1 into which the primary light is converted when the first light conversion member 76 is radiated with the primary light, and indirect irradiation type first light conversion light Y2 into which part of second light conversion light is converted when the first light conversion member 76 is radiated with the part of second light conversion light wherein the part of second light conversion light into which the primary light is converted when the second light conversion member 78 is radiated with the primary light, and is emitted from the region in the vicinity of the input part 68 to the detection light extractor 42. The operation determination circuit 50 determines the operation of the first and second light conversion members 76 and 78 based on the change amount of the detection light output signal output from the detection light extractor 42.

That is, in the endoscope illumination apparatus 12 according to the present embodiment, the operations of the first light conversion member 76 and the second light conversion member 78 are determined by the direct irradiation type first light conversion light Y1 and the indirect irradiation type first light conversion light Y2. In this way, it is possible to provide the endoscope illumination apparatus 12 capable of determining the operation of a plurality of light conversion members by detecting the amount of change of one light conversion light generated by the interaction of a plurality of light conversion members.

Both of the first and second light conversion members 76 and 78 are arranged on the optical axis of the primary light entering from the input part 68, and the first light conversion member 76 is disposed closer to the input part 68 than the second light conversion member 78. The first light conversion member 76 has a first fluorescent substance that absorbs at least part of the primary light and converts the primary light into a first fluorescent light having a wavelength range different from that of the primary light, and the second light conversion member 78 has a scattering or reflection member having a function of converting light distribution of at least part of the primary light laterally or rearwardly.

In this case, the operation determination circuit 50 has a function of calculating a detection light quantity standard value from the primary light source drive information when the primary light source 36 emits primary light, a function of setting a standard detection light range including the detection light quantity standard value, and a function of setting the first abnormality detection range and the second abnormality detection range by dividing the range outside the standard detection light range, and the operation determination circuit 50 includes an operation estimation circuit 52 that detects that range the detection light output signal is included in of the standard detection light range, the first abnormality detection range, and the second abnormality detection range, and based on the detection result estimates an operation of the first and second light conversion members 76 and 78.

In this manner, the first abnormality detection range (partial abnormality estimation range) and the second abnormality detection range (entire abnormality estimation range) obtained by dividing the quantity of the detection light into two with the threshold value (partial abnormality estimation threshold value) outside the standard detection light range are provided, whereby the level of abnormal operation can be divided into cases and estimated.

It should be noted that the first abnormality detection range exists within a predetermined difference from the standard detection light range, and in the case where the detection light output signal exists in the first abnormality detection range, the operation estimation circuit 52 estimates the operation as a partial abnormal operation that is an abnormal operation of any one of the first and second light conversion members 76 and 78.

In addition, the second abnormality detection range exists outside the predetermined difference from the standard detection light range, and the operation estimation circuit 52, when the detection light output signal exists in the second abnormality detection range, estimates the operation as an entire abnormal operation that is an abnormal operation of both of the first and second light conversion members 76 and 78.

In addition, in the endoscope illumination apparatus 12 according to the first embodiment, the first abnormality detection range exists within a predetermined difference from the standard detection light range, and the second abnormality detection range exists outside the predetermined difference from the standard detection light range. Then, the operation determination circuit 50 normalizes the value of the detection light output signal and the detection light quantity standard value based on the primary light source drive information, and the operation estimation circuit 52 estimates that the operation is a partial abnormal operation that is an abnormal operation of any one of the first and second light conversion members 76 and 78 when a normalized detection light output signal value exists in the first abnormality detection range, and estimates that the operation is an entire abnormal operation that is an abnormal operation of both of the first and second light conversion members 76 and 78 when the normalized detection light output signal value exists in the second abnormality detection range. Here, when the operation estimation circuit 52 estimates that the operation is the entire abnormal operation or the partial abnormal operation, the operation determination circuit 50 perform control so as to causes the primary light source 36 to emit the operation verification primary light that has lower quantity of light than that of the primary light. The detection light extractor 42 receives the verification detection light emitted from the light convertor 28 based on the operation verification primary light, and outputs the verification detection light output signal corresponding to the quantity of the verification detection light. The operation determination circuit 50 normalizes the value of the verification detection light output signal based on the primary light source drive information. Then, the operation determination circuit 50 further includes an abnormal operation determination circuit 54 that determines the entire abnormal operation or the partial abnormal operation depending on which range the normalized verification detection light output signal value exists in of the first abnormality detection range or the second abnormality detection range.

As described above, by performing the two-step determination in which the abnormal operation determination performed by using the primary light with a low quantity of light (safe quantity of light) at the time of abnormal operation estimation, it is possible to improve the determination accuracy of abnormal operation.

In this case, preferably the operation determination circuit 50 sets the quantity of the operation verification primary light to be low with respect to the primary light source 36 when the operation estimation circuit 52 estimates that the operation is an entire abnormal operation rather than when the operation estimation circuit 52 estimates that the operation is partial abnormal operation.

Further, when the estimation result by the operation estimation circuit 52 is identical to as the determination result by the abnormal operation determination circuit 54, the operation determination circuit 50 determines the identical result as a type of abnormal operation.

When the operation determination circuit 50 determines that the operation is the entire abnormal operation or the partial abnormal operation, preferably the operation determination circuit 50 performs control so that a quantity of the primary light is equal to or smaller than a quantity of the operation verification primary light with respect to the primary light source 36.

In addition, when the estimation result by the operation estimation circuit 52 is different from the determination result by the abnormal operation determination circuit 54, the operation determination circuit 50 selects the determination result by the abnormal operation determination circuit 54 as the determination result.

Alternatively, the operation determination circuit 50 further includes an abnormal operation member identification circuit 56 that identifies the type of abnormal operation of the first and second light conversion members 76 and 78 in the light convertor 28, and the abnormal operation member identification circuit 56 identifies a member of abnormal operation of at least one or both of the first and second light conversion members 76 and 78 on the basis of the amount of difference between the normalized detection light output signal value and the normalized verification detection light output signal value when the abnormal operation determination circuit 54 determines that the operation is the entire abnormal operation or the partial abnormal operation.

In this way, by extracting the difference between the amount of variation between the detection light and the verification detection light at the time of abnormal operation determination, a member in an abnormal operation of any one or both of the first and second light conversion members 76 and 78 (for example, a laminated structure) whose structures are specified in advance can be determined.

It should be noted that the first fluorescent substance has a predetermined temperature quenching characteristic and the abnormal operation member identification circuit 56 determines whether the type of abnormal operation is a temperature quenching of the first fluorescent substance based on whether the normalized verification detection light output signal value has increased more than a predetermined amount with respect to the normalized detection light output signal value.

In this way, by detecting whether the verification detection light increases by a predetermined amount with respect to the detection light at the time of abnormal operation determination, it is possible to detect the influence of the temperature quenching (that is, not a failure) of the first light conversion member 76.

In this case, when the normalized verification detection light output signal value has increased more than a predetermined amount with respect to the normalized detection light output signal value, the abnormal operation member identification circuit 56 identifies that the type of abnormal operation is a temperature quenching of the first fluorescent substance. When the abnormal operation member identification circuit 56 identifies that the type of abnormal operation is the temperature quenching of the first fluorescent substance, the operation determination circuit 50 performs control so as to cause the primary light source 36 to emit a quantity of primary light larger than a quantity of the operation verification primary light.

That is, since temperature quenching is not a failure, it is possible to allow a larger quantity of light than that of the operation verification light.

In addition, when the normalized verification detection light output signal value and the normalized detection light output signal value are substantially equal to each other, and the difference between them and the standard detection light range is smaller than the predetermined amount, the abnormal operation member identification circuit 56 identifies that the type of abnormal operation is an abnormal operation of the second light conversion member 78.

In this way, it is possible to determine the abnormal operation of the second light conversion member 78.

When the normalized verification detection light output signal value and the normalized detection light output signal value are substantially equal to each other, and the difference between them and the standard detection light range is larger than the predetermined amount, the abnormal operation member identification circuit 56 identifies that the type of abnormal operation is an abnormal operation of the first and second light conversion members 76 and 78.

In this way, it is possible to determine the abnormal operation of both the first and second light conversion members 76 and 78.

It should be noted that the direct irradiation type first light conversion light Y1 occupies a larger proportion of the detection light than the indirect irradiation type first light conversion light Y2.

Further, the first fluorescent substance can be a transparent fluorescent substance (ceramics) that transmits virtually without diffusion primary light that has not been absorbed.

In addition, in addition, a quantity of the second light conversion light that is emitted to the first fluorescent substance from the second light conversion member 78 is larger than a quantity of return light of primary light generated by the Fresnel reflection with respect to air on the emission surface of the first fluorescent substance.

Therefore, since the quantity of the detection light decreases due to the detachment of the second light conversion member, the desorption of the second light conversion member can be determined.

In addition, the detection light extractor 42 includes a light receiving element for receiving the detection light, and the light receiving surface of the light receiving element is disposed closer to the input part 68 side than an entrance surface of the first fluorescent substance that the primary light enters.

In this case, the endoscope illumination apparatus 12 further includes an optical coupler 40 having two input ends and one output end, and one input end of the optical coupler 40 is optically connected to the primary light source 36, The other input end of the optical coupler 40 is optically connected to the light receiving element and one output end of the optical coupler 40 is optically connected to the input part 68 of the light convertor 28 The optical coupler 40 has a function of guiding the primary light emitted from the primary light source 36 to the light convertor 28 and guiding the detection light from the light convertor 28 side toward the light receiving element side.

Here, the light receiving element has higher light receiving sensitivity in the wavelength range of the first fluorescent light than in the wavelength range of the primary light.

In addition, the endoscope system 10 according to the first embodiment includes the endoscope illumination apparatus 12 according to the first embodiment the imaging unit 30 that images the reflected light RL of the illumination light IL with which a predetermined irradiation area is irradiated, and an image processing circuit 62 that performs predetermined image processing based on an imaging signal imaged by the imaging unit 30 to acquire an image.

Therefore, it is possible to provide the endoscope system 10 capable of determining the operation of a plurality of light conversion members by detecting the amount of change of one light conversion light caused by the interaction of a plurality of light conversion members.

Alternatively, the endoscope system 10 according to the first embodiment includes an imaging unit 30 that images the reflected light RL of the illumination light IL with which a predetermined irradiation area is irradiated, and an image processing circuit 62 that performs predetermined image processing to acquire an image based on an imaging signal imaged by the imaging unit 30. The operation determination circuit 50 performs switching from the primary light to the operation verification primary light within a predetermined period so that the irradiation area of the illumination light IL by the primary light and the irradiation area of the illumination light IL by the operation verification primary light immediately after the switching are substantially equal to each other. The image processing circuit 62 acquires an image including at least common area among the images successively acquired by the illumination light IL with the primary light and the operation verification primary light.

As described above, in the endoscope system 10 including the imaging unit 30 and the image processing circuit 62, switching from the operation estimation circuit 52 to the abnormal operation determination circuit 54 can be performed within a continuous image acquisition period.

In this case, it is desirable that the image processing circuit 62 performs signal amplification on a imaging signal imaged by the operation verification primary light so as to correct the difference in the quantity of light between the primary light and the operation verification primary light to acquire an image.

Alternatively, the operation determination circuit 50 may control the imaging unit 30 so as to reduce an imaging frame rate of the imaging unit 30 before emitting the operation verification primary light, and may control the primary light source 36 so as to emit the operation verification primary light within a non-exposure period of the imaging unit 30.

In the first embodiment, the optical coupler 40 is of the 2-input 1-output type. The optical coupler 40 of the 2-input 2-output type is used, and the second light convertor, similar to the light convertor 28, can be connected to another output end. That is, the endoscope apparatus 14 may have two light convertors.

Further, not limited to the optical coupler 40, an optical element such as a half mirror may be disposed between the primary light source 36 and the light convertor 28 as a component for branching the light.

Further, the detection light detected by the detection light extractor 42 may detect a light component obtained by combining the first fluorescent light and the primary light B1.

Further, a small amount of diffusing member may be placed in the first light conversion member 76 so as to become smaller than the light distribution angle conversion amount of the second light conversion member 78.

Further, the first light conversion member 76 and the second light conversion member 78 may be spaced apart on the optical axis of the primary light B1. In this case, a light transmission member may be disposed between the first light conversion member 76 and the second light conversion member 78, or an air layer may be provided between the first light conversion member 76 and the second light conversion member 78. Furthermore, a mixed layer of the first light conversion member 76 and the second light conversion member 78 may exist between the first light conversion member 76 and the second light conversion member 78.

[Modification]

It should be noted that the first and second light conversion members 76 and 78 may not have the same coaxial shape.

Figure 10:
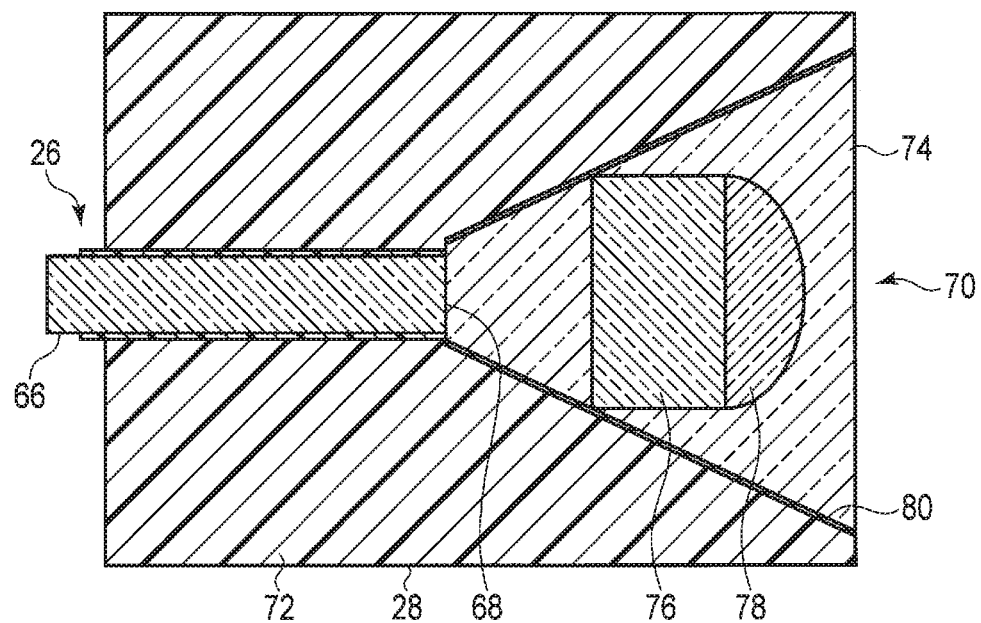
FIG. 10 is a cross-sectional view showing a constitution example of a light convertor in a modification of a first embodiment.

For example, as shown in FIG. 10, the emitting side of the second light conversion member 78 may have a hemispherical shape.

Figure 11:
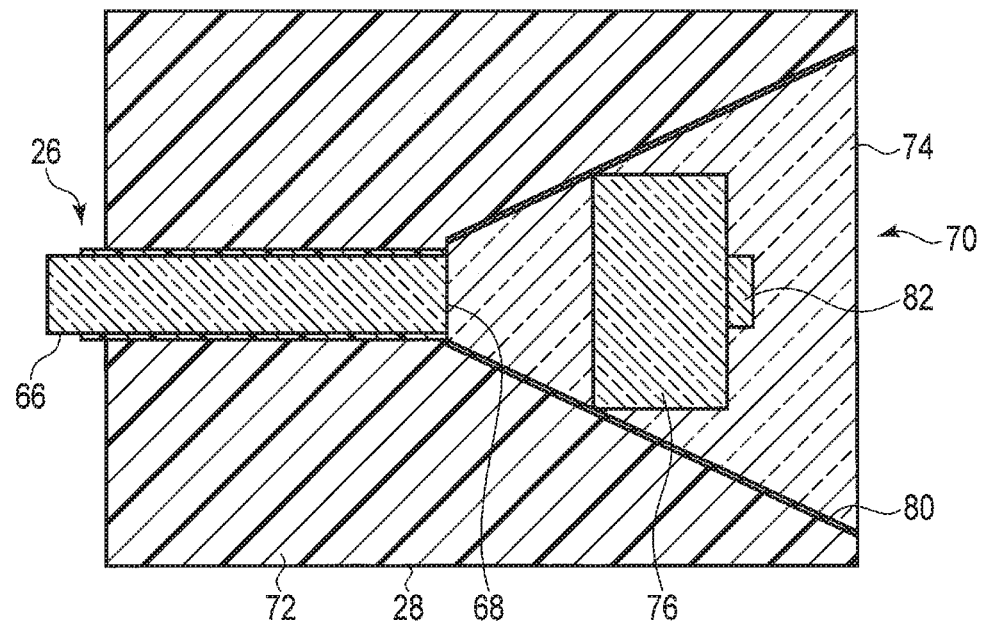
FIG. 11 is a cross-sectional view showing another constitution example of the light convertor in a modification of the first embodiment.

Further, as shown in FIG. 11, as the second light conversion member 78, a reflection member 82 that is a reflecting mirror that reflects the primary light only on the optical axis of the primary light on the emitting side of the first light conversion member 76, and transmits the first fluorescent light may be disposed.

As described above, in this modification, by reducing scattering or reflection members of the peripheral portion, it is possible to reduce the proportion of the first fluorescent light scattered or reflected in the light convertor 28 and to increase the amount of emitting the first fluorescent light as the illumination light IL.

Second Embodiment

Next, a second embodiment of the present invention will be described. Here, the differences from the above-described first embodiment will be described, and the same parts will be denoted by the same reference numerals and description thereof will be omitted.

Figure 12:
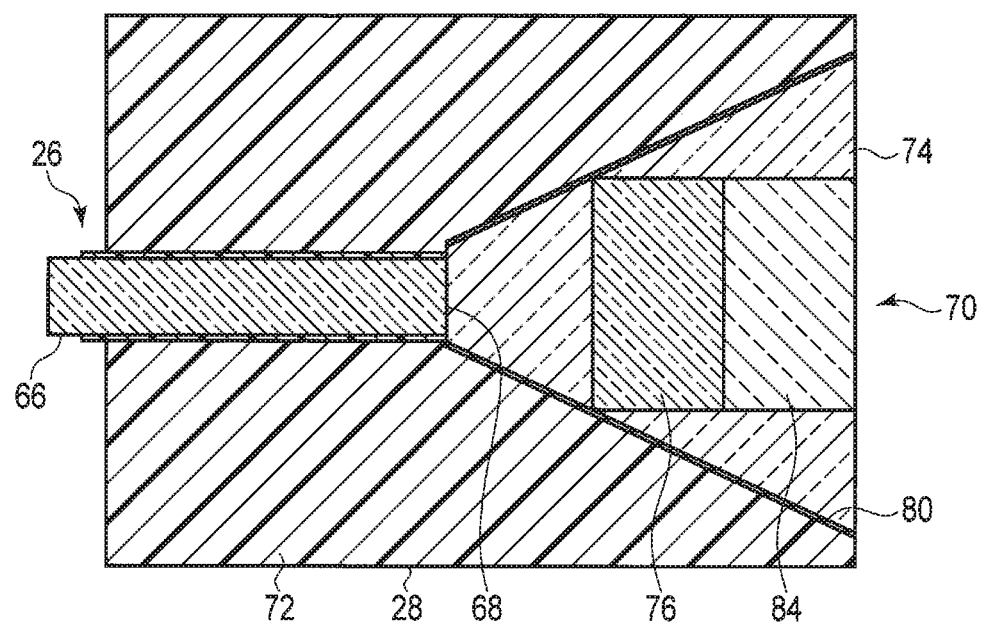
FIG. 12 is a cross-sectional view showing an example of a constitution of a light convertor in an endoscope system including an endoscope illumination apparatus according to a second embodiment of the present invention.

In the second embodiment, as shown in FIG. 12, the light convertor 28 includes a second light conversion member 84 instead of the second light conversion member 78 of the first embodiment. The second light conversion member 84 has a diffusing member that is the same scattering or reflection member as the second light conversion member 78 and further absorbs the primary light, and has a second fluorescent substance (red) that emits light on the longer wavelength side than the first fluorescent light.

Figure 13:
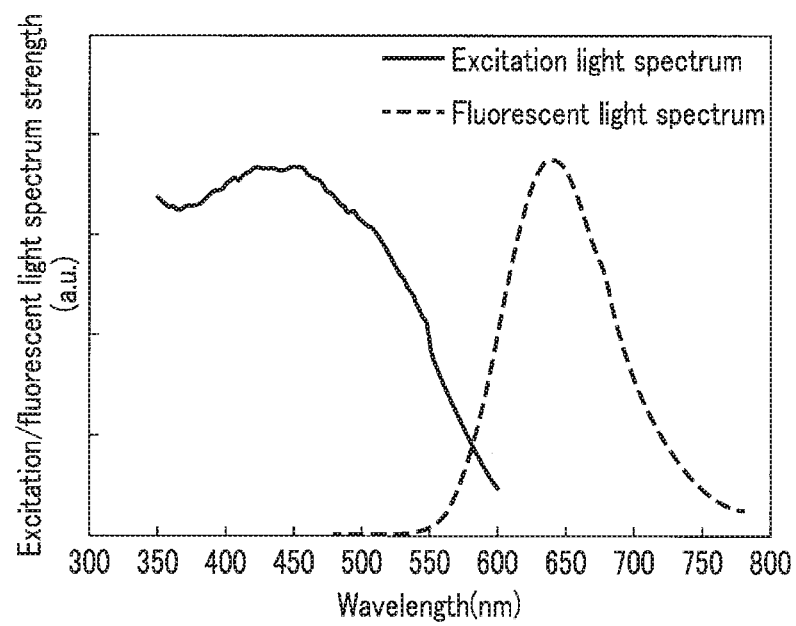
FIG. 13 is a diagram showing an example of optical characteristics of the second light conversion member in the light convertor.

This second fluorescent substance has a fluorescent light spectrum as indicated by a broken line with respect to the excitation light spectrum as indicated by the solid line in FIG. 13. Therefore, the second light conversion member 84 absorbs the primary light (blue laser light) emitted from the primary light source 36, and has properties that perform wavelength-conversion into the second fluorescent light that is light having a longer wavelength than the primary light. The second fluorescent substance absorbs the primary light in the blue wavelength range and performs wavelength-conversion into red fluorescent light. Therefore, the secondary light includes the second fluorescent light (red).

In the light convertor 28 having the second light conversion member 84, when the primary light B1 enters it, in addition to the first fluorescent light (the direct irradiation type first light conversion light Y1 and the indirect irradiation type first light conversion light Y2), second fluorescent light is also generated, so that at least part of the second fluorescent light enter the optical fiber 26 as return light.

However, since the second light conversion member 84 is located on the emitting side relative to the first light conversion member 76, the quantity of return light of the second fluorescent light is smaller than that of the return light of the first fluorescent light.

As described above, in the endoscope illumination apparatus 12 and the endoscope system 10 according to the second embodiment, a second light conversion member 84 includes a second fluorescent substance that absorbs at least part of the primary light and converts the primary light into second fluorescent light having a wavelength range different from that of the primary light and the second fluorescent light, and the first fluorescent light occupies a larger proportion of the detection light than the second fluorescent light.

Therefore, in addition to the first fluorescent light, the second fluorescent light can also be used as the detection light, and the light receiving sensitivity of the detection light can be enhanced.

For example, when a second light conversion member 84 is detached, the difference from the detection light at the normal time increases, and abnormal operation of only the second light conversion member 84 can be easily determined.

Note that the second light conversion member 84 may further include a first fluorescent substance. By doing so, the difference of the detection light is further increased by detachment of the second light conversion member 84.

In addition, in the second embodiment, as in the first embodiment, the first and second light conversion members 76 and 84 may not be coaxial or identical in shape.

Third Embodiment

Next, a third embodiment of the present invention will be described. Here, the differences from the above-described first embodiment will be described, and the same parts will be denoted by the same reference numerals and description thereof will be omitted.

Figure 14:
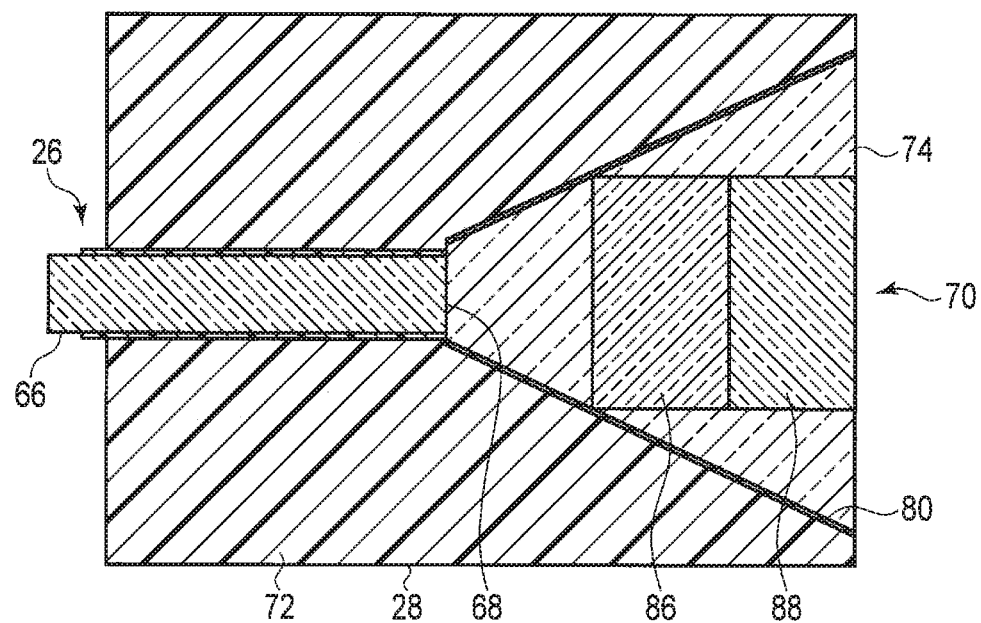
FIG. 14 is a cross-sectional view showing a constitution example of a light convertor according to a third embodiment of the present invention.

In the third embodiment, as shown in FIG. 14, the light convertor 28 includes the first light conversion member 86 instead of the first light conversion member 76 of the first embodiment, and a second light conversion member 88 instead of the second light conversion member 78.

The second light conversion member 88 has a diffusing member that is the same scattering or reflection member as the second light conversion member 78 and further absorbs the primary light, and has a second fluorescent substance (green) that emits light on the shorter wavelength side than the first fluorescent light.

Figure 15:
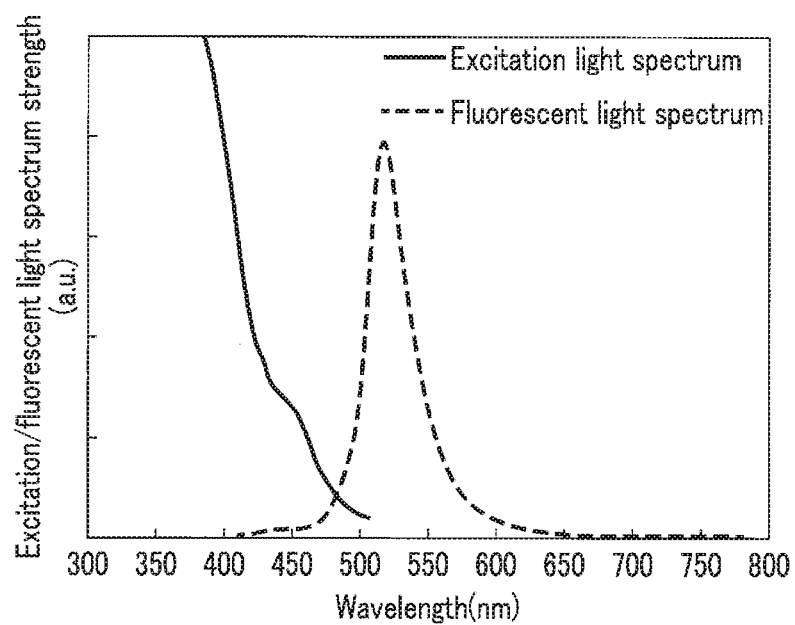
FIG. 15 is a diagram showing an example of optical characteristics of a second light conversion member in the light convertor of the third embodiment.

This second fluorescent substance has a fluorescent light spectrum as indicated by a broken line with respect to the excitation light spectrum as indicated by the solid line in FIG. 15. Therefore, the second light conversion member 88 absorbs the primary light (blue laser light) emitted from the primary light source 36, and has properties that perform wavelength-conversion into the second fluorescent light that is light having a longer wavelength than the primary light and having a shorter wavelength than the first fluorescent light. The second fluorescent substance absorbs the primary light in the blue wavelength range and performs wavelength-conversion into green fluorescent light. Therefore, the secondary light includes the second fluorescent light (green).

In addition, the first light conversion member 86 further has the property of absorbing such second fluorescent light and emitting the first fluorescent light.

In the light convertor 28 having the first and second light conversion members 86 and 88, when the primary light B1 enters the light convertor 28, in addition to the first fluorescent light (the direct irradiation type first light conversion light Y1 and the indirect irradiation type first light conversion light Y2), second fluorescent light is also generated by the second light conversion member 88, so that at least part of the second fluorescent light enter the optical fiber 26 as return light.

Further, the second fluorescent light is absorbed (secondarily absorbed) into the first fluorescent substance of the first light conversion member 86 and emitted as the first fluorescent light, and at least part thereof enters the optical fiber 26 as return light.

However, since the second light conversion member 88 is located on the emitting side relative to the first light conversion member 86, the quantity of return light of the second fluorescent light is smaller than that of return light of the first fluorescent light.

As described above, in the endoscope illumination apparatus 12 and the endoscope system 10 according to the third embodiment, the first fluorescent substance of the first light conversion member 86 absorbs at least part of the second fluorescent light, and converts it to the first fluorescent light.

Therefore, in addition to the first fluorescent light of direct irradiation and indirect irradiation, the first fluorescent light due to secondary absorption can also be used as detection light, and the light receiving sensitivity of the detection light can be enhanced.

For example, when a second light conversion member 88 is detached, the difference from the detection light at the normal time increases, and abnormal operation of only the second light conversion member 88 can be easily determined.

Also in the third embodiment, as in the first embodiment, the first and second light conversion members 86 and 88 may not be coaxial or identical in shape.

Although the present invention has been described based on the embodiments, the present invention is not limited to the above-described embodiments, and it is obvious that various modifications and applications can be made within the scope of the gist of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope illumination apparatus comprising:
    a light convertor including first and second light conversion materials arranged in series to receive primary light emitted from a primary light source and convert first and second optical properties, respectively, of the primary light, the first optical property being a wavelength conversion and the second optical property being other than a wavelength conversion;
    a detector that receives at least part of first light conversion light converted by the first light conversion material as detection light, and outputs a detection signal corresponding to a quantity of the detection light, the detector including a light quantity sensor; and
    a controller configured to estimate, based on an amount of change in the detection signal output from the detector, whether any one of the first and second light conversion materials is in an abnormal operation or whether both of the first and second light conversion materials are in an abnormal operation.

2. The endoscope illumination apparatus according to claim 1,
    further comprising the primary light source,
    wherein the light convertor converts the primary light into secondary light having an optical characteristic different from that of the primary light and emits at least part of the secondary light as the detection light and illumination light,
    wherein the light convertor has an input part in which the primary light enters,
    wherein the detection light is light emitted from a region in the vicinity of the input part to the detector,
    wherein the detection light includes at least one of
    direct irradiation type first light conversion light into which the primary light is converted by the first light conversion material radiated with the primary light, and
    indirect irradiation type first light conversion light into which part of second light conversion light is converted by the first light conversion material radiated with part of the second light conversion light, the primary light being converted into the second light conversion light by the second light conversion material radiated with the primary light.

3. The endoscope illumination apparatus according to claim 2,
    wherein both the first and second light conversion materials are disposed on an optical axis of the primary light entering from the input part, and the first light conversion material is disposed closer to the input part than the second light conversion material,
    wherein the first light conversion material has a first fluorescent substance that absorbs at least part of the primary light and converts the primary light into a first fluorescent light having a wavelength range different from that of the primary light, and
    wherein the second light conversion material includes a scattering or reflection member having a function of converting light distribution of at least part of the primary light laterally or rearwardly.

4. The endoscope illumination apparatus according to claim 3,
    wherein the controller includes a function of calculating a detection light quantity standard value from primary light source drive information when the primary light source emits the primary light, a function of setting a standard detection light range including the detection light quantity standard value, and a function of setting a first abnormality detection range and a second abnormality detection range by dividing a range outside the standard detection light range, and
    wherein the controller detects which range the detection signal is included in of the standard detection light range, the first abnormality detection range, and the second abnormality detection range, and based on the detection result estimate an operation of the first and second light conversion materials.

5. The endoscope illumination apparatus according to claim 4,
    wherein the first abnormality detection range exists within a predetermined difference from the standard detection light range, and wherein when the detection signal exists in the first abnormality detection range, the controller estimates that the operation is a partial abnormal operation that is an abnormal operation of any one of the first and second light conversion materials.

6. The endoscope illumination apparatus according to claim 4,
wherein the second abnormality detection range exists outside a predetermined difference from the standard detection light range, and
wherein when the detection signal exists in the second abnormality detection range, the controller estimates that the operation is an entire abnormal operation that is an abnormal operation of both of the first and second light conversion materials.

7. The endoscope illumination apparatus according to claim 4,
wherein the first abnormality detection range exists within a predetermined difference from the standard detection light range,
wherein the second abnormality detection range exists outside the predetermined difference from the standard detection light range,
wherein the controller normalizes a value of the detection signal and the detection light quantity standard value based on the primary light source drive information,
wherein the controller estimates that the operation is a partial abnormal operation that is an abnormal operation of any one of the first and second light conversion materials, when a normalized detection light output signal value exists in the first abnormality detection range, and estimates that the operation is an entire abnormal operation that is an abnormal operation of both of the first and second light conversion materials when the normalized detection light output signal value exists in the second abnormality detection range,
wherein when the controller estimates that the operation is the entire abnormal operation or the partial abnormal operation,
the controller performs control so as to causes the primary light source to emit operation verification primary light with a lower quantity of light than a quantity of the primary light,
the detector receives verification detection light emitted from the light convertor based on the operation verification primary light and outputs verification detection light output signal corresponding to a quantity of the verification detection light, and
the controller normalizes a value of the verification detection light output signal based on the primary light source drive information, and
wherein the controller is further configured to determine the entire abnormal operation or the partial abnormal operation depending on which range the normalized verification detection light output signal value exists in of the first abnormality detection range and the second abnormality detection range.

8. The endoscope illumination apparatus according to claim 7,
wherein the controller sets a quantity of the operation verification primary light to be low with respect to the primary light source when the controller estimates that the operation is an entire abnormal operation rather than when the controller estimates that the operation is partial abnormal operation.

9. The endoscope illumination apparatus according to claim 7,
wherein the controller further includes an abnormal controller configured to identify a type of abnormal operation of the first and second light conversion materials in the light convertor, and
wherein the controller identifies a member that is in an abnormal operation of at least one or both of the first and second light conversion materials based on an amount of difference between the normalized detection light output signal value and the normalized verification detection light output signal value when the controller determines that the operation is the entire abnormal operation or the partial abnormal operation.

10. The endoscope illumination apparatus according to claim 9,
wherein the first fluorescent substance has a predetermined temperature quenching characteristic, and
wherein the controller determines whether the type of abnormal operation is a temperature quenching of the first fluorescent substance based on whether the normalized verification detection light output signal value has increased more than a predetermined amount with respect to the normalized detection light output signal value.

11. The endoscope illumination apparatus according to claim 9,
wherein when the normalized verification detection light output signal value and the normalized detection light output signal value are substantially equal to each other, and a difference between the normalized verification detection light output signal value and normalized detection light output signal value and the standard detection light range is smaller than a predetermined amount, the controller identifies that the type of the abnormal operation is an abnormal operation of the second light conversion material, or
wherein when the normalized verification detection light output signal value and the normalized detection light output signal value are substantially equal to each other, and a difference between the normalized verification detection light output signal value and normalized detection light output signal value and the standard detection light range is larger than a predetermined amount, the controller identifies that the type of abnormal operation is an abnormal operation of the first and second light conversion materials.

12. The endoscope illumination apparatus according to claim 3,
wherein the direct irradiation type first light conversion light occupies a larger proportion of the detection light than the indirect irradiation type first light conversion light.

13. The endoscope illumination apparatus according to claim 3,
wherein the first fluorescent substance absorbs at least part of the second fluorescent light and converts the absorbed second fluorescent light into first fluorescent light,
wherein the second light conversion material further includes a second fluorescent substance that absorbs at least part of the primary light and converts the primary light into second fluorescent light having a wavelength range different from that of the primary light and the first fluorescent light, and wherein the first fluorescent light occupies a larger proportion of the detection light than the second fluorescent light.

14. The endoscope illumination apparatus according to claim 3,
wherein the detector includes a light receiving element configured to receive the detection light, and
wherein a light receiving surface of the light receiving element is disposed closer to the input part than an entrance surface of the first fluorescent substance that the primary light enters.

15. The endoscope illumination apparatus according to claim 14,
further comprising an optical coupler having two input ends and one output end,
wherein one input end of the optical coupler is optically connected to the primary light source,
wherein the other input end of the optical coupler is optically connected to the light receiving element,
wherein the one output end of the optical coupler is optically connected to the input part of the light convertor, and
wherein the optical coupler has a function of guiding the primary light emitted from the primary light source to the light convertor and guiding the detection light from the light convertor side toward the light receiving element side.

16. The endoscope illumination apparatus according to claim 15,
wherein the light receiving element has a light receiving sensitivity higher in a wavelength range of the first fluorescent light than in a wavelength range of the primary light.

17. An endoscope system comprising:
the endoscope illumination apparatus according to claim 2;
an imaging unit configured to image reflected light of the illumination light with which a predetermined irradiation area is irradiated; and
the controller is configured to perform predetermined image processing based on a imaging signal imaged by the imaging unit to acquire an image.

18. An endoscope system comprising:
the endoscope illumination apparatus according to claim 7;
an imaging unit configured to image reflected light of the illumination light with which a predetermined irradiation area is irradiated; and
the controller is configured to perform predetermined image processing based on a imaging signal imaged by the imaging unit to acquire an image,
wherein the controller performs switching from the primary light to the operation verification primary light within a predetermined period so that an irradiation area of the illumination light by the primary light and an irradiation area of the illumination light by the operation verification primary light immediately after the switching is substantially equal to each other, and
wherein the controller acquires an image including at least a common area among images successively acquired by the illumination light of the primary light and the operation verification primary light.

19. The endoscope system according to claim 18,
wherein the controller performs signal amplification on a imaging signal imaged by the operation verification primary light so as to correct a difference in a quantity of light between the primary light and the operation verification primary light to acquire an image.

20. The endoscope system according to claim 18,
wherein the controller controls the imaging unit so as to cause the imaging unit to reduce an imaging frame rate of the imaging unit before emitting the operation verification primary light, and
wherein the controller controls the primary light source so as to cause the primary light source to emit the operation verification primary light within a non-exposure period of the imaging unit.

* * * * *